United States Patent [19]

Clarke et al.

[11] Patent Number: 4,863,268

[45] Date of Patent: * Sep. 5, 1989

[54] DIFFRACTOSIGHT IMPROVEMENTS

[75] Inventors: Donald A. Clarke; Rodger Reynolds, both of Windsor; Timothy R. Pryor, Tecumseh, all of Canada

[73] Assignee: Diffracto Ltd., Windsor, Canada

[*] Notice: The portion of the term of this patent subsequent to Dec. 16, 2003 has been disclaimed.

[21] Appl. No.: 33,930

[22] Filed: Apr. 2, 1987

Related U.S. Application Data

[63] Continuation of Ser. No. 711,646, Mar. 14, 1985, abandoned, which is a continuation-in-part of Ser. No. 579,971, Feb. 14, 1984, Pat. No. 4,629,319.

[51] Int. Cl.$^4$ .................... G01N 21/88; G01N 21/89; G01N 21/90
[52] U.S. Cl. .................................... 356/237; 356/445; 358/106
[58] Field of Search ................. 356/237, 445; 358/106

[56] References Cited

U.S. PATENT DOCUMENTS

| 3,734,626 | 5/1973 | Roberts et al. | 356/237 X |
| 3,892,494 | 7/1975 | Baker et al. | 356/237 X |
| 4,207,467 | 6/1980 | Doyle | 356/382 X |
| 4,629,319 | 12/1986 | Clarke et al. | 356/237 |

Primary Examiner—Vincent P. McGraw
Attorney, Agent, or Firm—Larson and Taylor

[57] ABSTRACT

Disclosed are improvements in the surface inspection method and apparatus invention of our copending application "Panel Surface Flaw Inspection", Ser. No. 579,971, U.S. Pat. No. 4,629,319, which has now come to be described as "DiffractoSight". Particularly disclosed are semi and full automatic techniques for quantifying and locating localized surface distortions. Applications for determination of scratches, paint finish defects and other surface problems are also described.

The primary area of application is to cosmetic defects on automobile bodies, appliances, and furniture, and the dies, molds and models and other surfaces used in their manufacture.

81 Claims, 15 Drawing Sheets

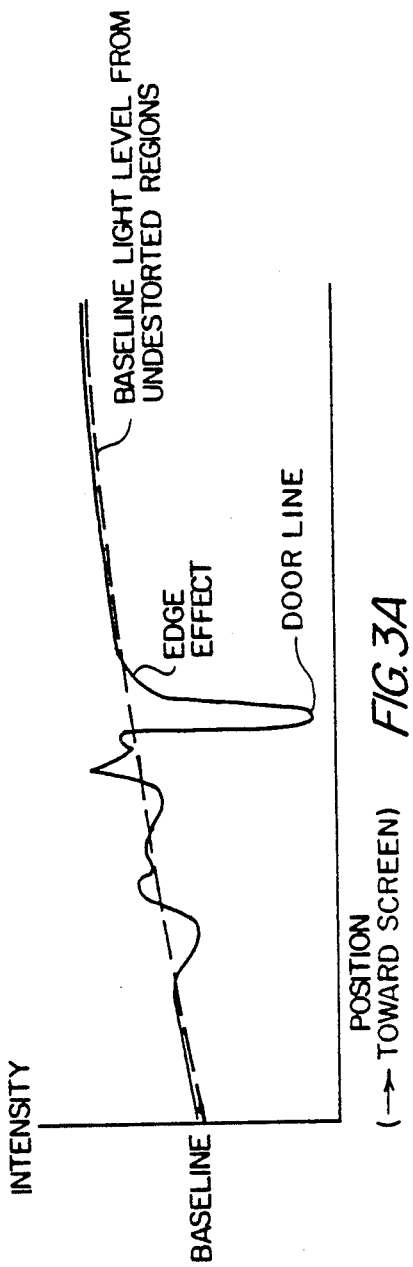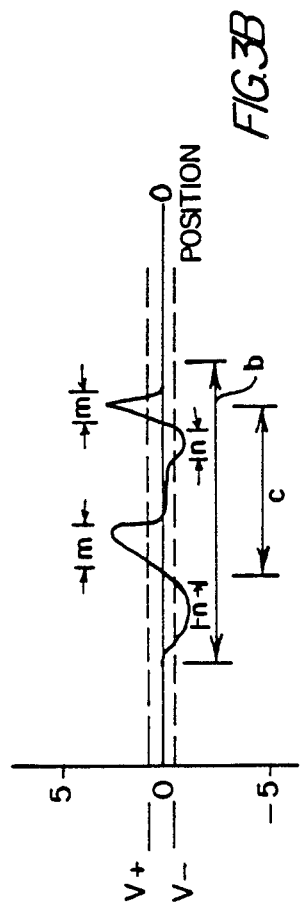

DIFFRACTOSIGHT IMPROVEMENTS

CROSS REFERENCE TO RELATED APPLICATIONS

This application is a continuation of application Ser. No. 711,646, filed Mar. 14, 1985, now abandoned, which was a continuation-in-part of application Ser. No. 579,971, filed Feb. 14, 1984, now U.S. Pat. No. 4,629,319.

BACKGROUND

In the course of practicing the copending invention, Panel Surface Flaw Inspection, U.S. Ser. No. 579,971, U.S. Pat. No. 4,629,319, to which this application is a continuation in part, we have found the embodiments of FIGS. 6–8A thereof (wherein an area of, in general, a substantial portion of an object is illuminated) to be by far the most potentially useful aspect to date of the invention since it provides a whole field area view of the object distortion, and the increased comprehension which results.

This application addresses useful aspects of the invention including means for automatically locating and quantifying defects.

The general field of application of this invention applies primarily to inspection of objects such as auto bodies, auto body panels, furniture, aircraft, etc. for cosmetic or funtional defects on exterior or other surfaces which need to present a uniformly contoured appearance free of localized defects in form. "DiffractoSight", a name coined for the embodiments of FIGS. 6, 7 and 8A of the referenced invention, is extremely powerful in analyzing such defects. The unique images of surfaces and the magnified distortions thereon provided by the invention are called herein DiffractoSight images.

This invention is illustrated in the embodiments herein which are:

FIGS. 1A, 1B, and 1C illustrate DiffractoSight images of painted car body sides at two different magnifications according to the invention. Images from unpainted surfaces which have been oiled or wetted to improve their surface reflectivity are effectively the same.

FIG. 3A and 3B illustrate, respectively, an intensity vs position scan through the image of FIG. 1 and a quantification by defect gray scale variation.

DETAILED DESCRIPTION OF THE PREFERRED EMBODIMENT

Figure 1A:
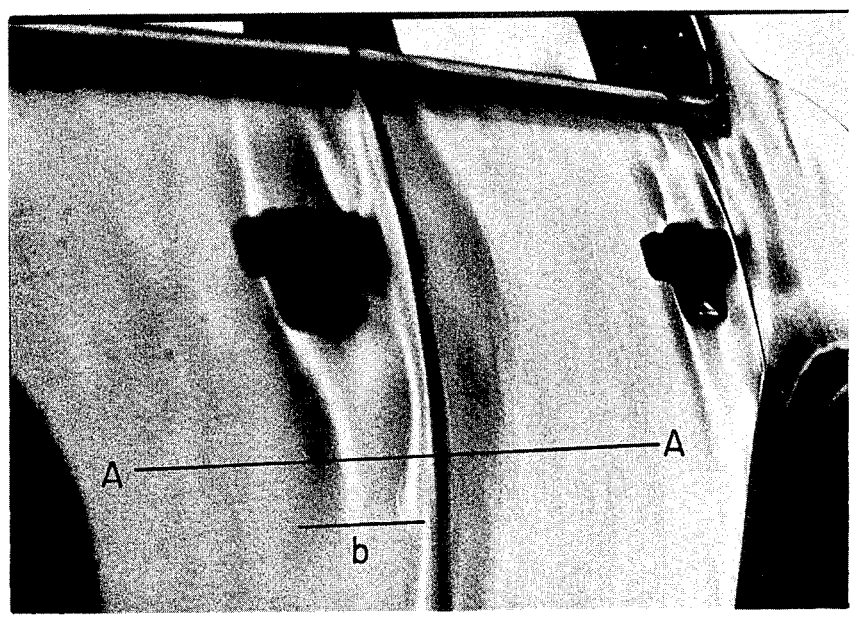
Figure 1B:
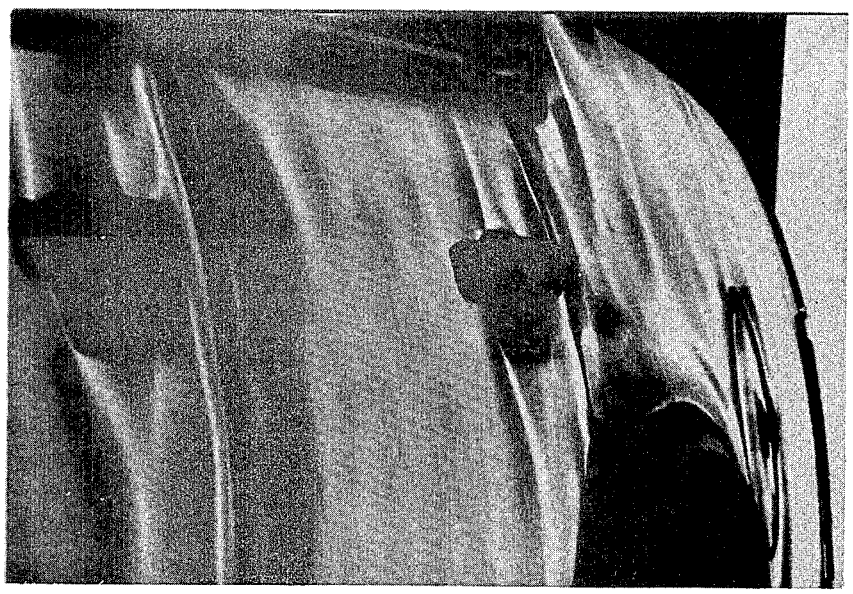
Figure 1C:
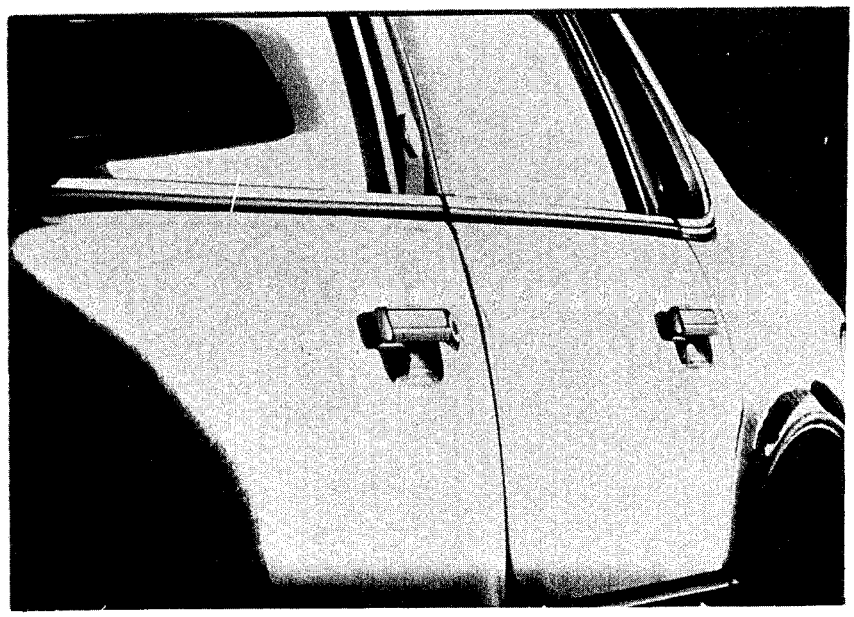
Figure 8A:
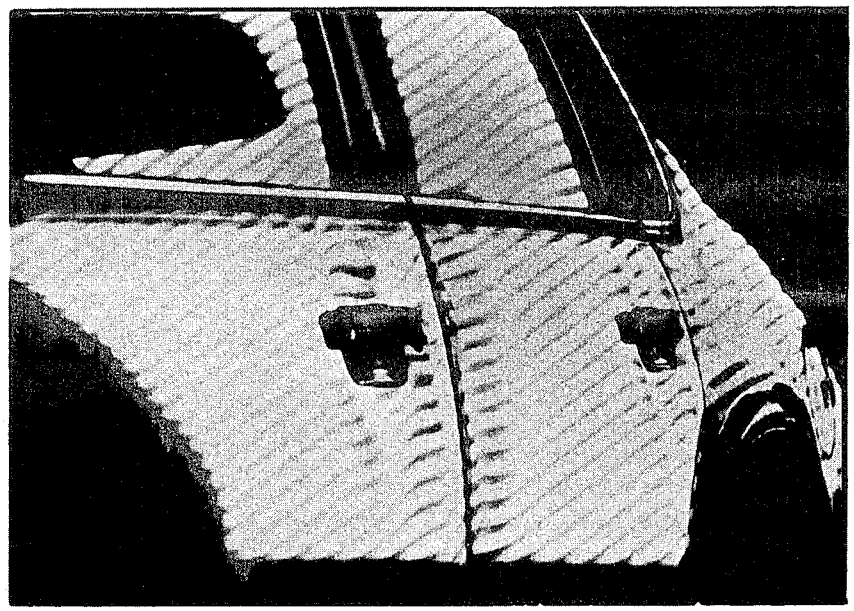
FIG. 8A illustrates a grid based defect analysis by contour line variation, optionally utilized as an overlaid contour grid with DiffractoSight image of FIG. 1.

FIGS. 1A and 1B are photographs of a typical painted new 1984 Pontiac STE body side at two magnification levels (135 mm and 270 mm focal length lenses) taken by using the basic invention of the referenced copending application in the form shown in FIG. 8A thereof (and schematically illustrated in FIG. 2A herein) with the light source placed off the camera axis in the direction of the part surface. FIG. 1C illustrates an over exposed example of the same shot as FIG. 1A.

Figure 2A:
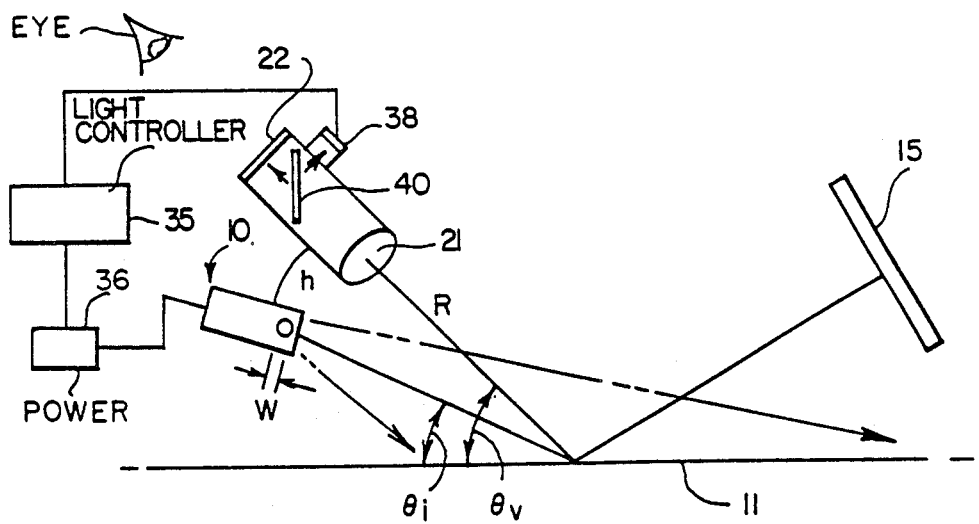
FIGS. 2A and 2B illustrate apparatuses used to obtain the "DiffractoSight" images of FIG. 1.

FIG. 2A illustrates the sensor parameters used to take the pictures of FIGS. 1A, 1B, and 1C. As shown, light source 10 illuminates surface 11 such that light reflected from said surface strikes screen 15 where it is re-reflected via said surface to camera 20 comprising lens 21 and, in this example, maxtrix photo detector 22. Alternatively, other detectors can be used, for example, photographic film, vidicons, mechanically swept linear arrays, etc. Pyroelectric vidicons can be used, for example, where infra red rather than visible radiation is employed.

In the example shown, the viewing camera is located at an angle to the surface $\theta v$ slightly grater than that of the incident light source, $\theta i$. Typically, a 35 mm camera with a 135mm lens located at a distance $R=3$ meters is used, with the light source offset a distance h of 30 mm. This small difference in angle is sufficient to produce the shadows shown in the photo. It is also sufficient to allow the image to be formed using the returned light from retro-reflective materials (see below).

In practicing the invention, we have found that the "shadow" producing version shown in FIG. 2A and also in FIG. 8A of the referenced parent application produces dramatically realistic images (shown in FIGS. 1A, 1B, and 1C), where the minute undulations of the surface create, in a magnified manner, apparent shadows and bright zones indicative of an apparent large light source located at the screen. The relation is apparently correct with "dark" indicating a "shadow" due to a surface slope depression facing away from the apparent light source (intercepting lens flux) and "light" on surface facing toward apparant the apparant light source (intercepting more flux). Images made by this technique are called "DiffractoSight images" in this disclosure.

If $\theta i > \theta v$, that is the light source is farther away in angle than the imaging camera (eye, etc.) from the surface, the darks and brights invert and it appears the correct relationship from a flux intercept point of view is as if the light source is near the camera—generally not as realistic to a human observer who realizes the screen is present (which seems like a larger light source).

For $\theta i = \theta v$, the apparent shadows and brights are reduced. A variation is noticed relative to the background, where local distortion of the surface occurs.

Typically, photographs such as FIG. 1A, 1B, and 1C have been shot at angles $\theta$ of roughly 20 to 30 degrees to the panel but even at 40 degrees or more, results have been obtained. It should stand to reason that the higher angles might give a little better response. The contrast though seems to degrade as higher angles $\theta$ are employed, but the image in some cases is more intelligible. One doesn't, at the higher angles, see the effects at the panel edges as pronounced as at the low angles (there is inevitably surface roll-off at stamped panel edges, which in many cases, is not of interest).

At the higher angles $\theta$, one sees less of a side of a car, for example, in any one view using the same optical magnification. However, less fore shortening occurs which could be beneficial.

We have found it generally desirable to focus the lens system of the camera to keep both the panel surface and the screen in focus (e.g. object plane at surface with sufficiently large depth of field, or object plane between surface and screen). Clearly, the FIGS. 1A, 1B, and 1C photographs indicate an in focus sharp surface condition.

For film camera exposure, it is often desirable to use a camera (e.g. an Olympus OM1) that allows automatic flash exposure using light detected from the film plane under all conditions using light along the lens axis. On-axis exposure control is useful for TV cameras too. Due to the angular distribution properties of the light returned by the retro-reflective screens, a 10 degree, let us say, angular variation between light source and camera, can cause a large reduction in light level vis a vis a zero degree (on-axis) situation where the camera is centered on the maximum of returned light intensity. It is useful to have an encoder on the camera as well to allow the date, time, etc. to be put on the pictures (or in the TV case, a stored video image).

For example, consider light controller 35 controlling the power supply 36 of light 10 in response to input from detector 38 receiving on-axis returned light from the part surface 11 via beam splitter 40. To provide a normalized situation part after part, the light is controlled in power such that the detected return is substantially the same from each part, independent of surface color, texture, dirty optics, light power degradation and the like. Where flashed light sources are used, the duration of the flash can be controlled to make the total amount of energy falling on the detector constant.

An alternate system keeps light power constant and varies the integration time of the detector (exposure time, if film) in inverse proportion to returning light power detected by detector 38.

One of the big advantages of DiffractoSight relative to the normal hilight booth/green room check setup employing florescent lights typically used in automotive plants is that with DiffractoSight you see the part surface over a large area as it is, without watching "edges" of fluorescent lights deviate due to variations in curvature of the part (which requires concentration on minute zones, a slow tedious demanding task).

DiffractoSight is therefore a major development as it allows people to see things they never could see before, and allows everybody to see them, in one view, in essentially the same way. This is vastly better than the fluorescent lights of the green room or show room where one has to move around, look from different views, move one's head, etc. to see anything. Even then it is extremely subjective using conventional techniques, and many arguments are generated and much training is required.

The DiffractoSight phenomena as shown in FIGS. 1A, 1B, and 1C is made to order for an operation with TV cameras, film, and the like, and is absolutely breathtaking to people in the die, sheet metal and plastic trade. Recently, the use of superimposed grid patterns projected with the same DiffractoSight light source (see FIG. 8) showed the distorted grid lines superimposed on the "shadows" of the DiffractoSight image. As near as has been determined to date, the grid line deviations and the shadowing both correspond to the degree of distortion, i.e. bearing out the fact that the shadows accurately describe the surface, or conversely, if one believes the shadows, then the grid lines give the quantified data.

For best results, a good grade of retro-reflective screen such as 3M Company "Scotchlite" 7615 or 7610 is desirable. Indeed, it is often necessary in many plant applications in the presence of ambient light. This material is composed of glass beads of relatively uniform dimension (40-75 microns dia.) randomly and closely distributed in an adhesive matrix. It typically returns most light along the axis of light incidence with light power diminished by half as one goes ±one-half degree from this axis. At ±2 degrees, returned power goes down by a factor of approximately 50.

With less effectiveness, spray on coatings of glass bead elements in random distribution can be used such as "Scotchlite" paint.

Specialized prismatic retro-reflectors such as "Reflexsite AC 1000" prismatic reflective sheeting, often having even more efficiency than glass bead screens, generally do not work as well. The method of retro-reflection is more structured (compared to the random glass bead screen) and imparts its own structure on the image.

As the degree of reflectiveness decreases due to fewer beads, the efficiency goes down and the DiffractoSight effect becomes more difficult to view. Where no beads are present, e.g. on a white diffuse screen (such as a piece of white paper even), elements of the effect appear to be observable in a dark room condition, but contrast and power are so low as to be effectively unuseable.

A key element in making the effect visible in this circumstance and in obtaining best results in all circumstances, is to use a substantially "point" light source of small dimension 'W' near the camera. We have found that the smaller the source dimension (in both planes), the better the DiffractoSight image contrast. However, something larger than a very small point can be used. For example, the photographs of FIGS. 1A, 1B, and 1C were taken with the FIG. 2A arrangement using a linear Xenon photographic flashlamp, ⅛" (3 mm) dia. (dimension 'W') apertured to be ½" (12 mm) long with the long axis oriented approximately parallel to the surface of the car body.

It is noted, however, that the use of an aperture on the flash gun in taking the pictures of FIGS. 1A, 1B, and 1C doesn't appear to make a vast difference. In other words, the normal linear flash lamp size about 1-1.5" (25-40 mm) in length, works nearly as well as one a half inch in length. In general, however, the smaller the source, the more clarity results. Generally the camera lens aperture should preferably be such as to maintain both the screen and surface in focus.

Automation of Image Readout

In this application, we desire to show practical application examples of the invention to car and other product manufacture, as well as method and apparatus for automating the readout of the "DiffractoSight" images obtained Automation allows unattended operation, but more importantly removes the remaining subjectivity of visual analysis by precisely, and consistently quantifying the severity of defects detected We have found that such automation can be provided in two ways—grid contour deviation and gray level image analysis. In some instances, both are desirably used; for example, gray level analysis to find or classify the defect by type, and dimensional deviation of grid images to quantify it. Alternatively, quantification can occur by matching the test gray level or grid image to known defect condition images, or by analyzing the variations in gray level light intensity.

Gray level image operations which are useful are, for example, image subtraction where a standard DiffractoSight image of the same surface (e.g. a door panel) or sections thereof is compared to one or more standard images (for example, taken on good, bad and marginal panel sections) and the closest match obtained (as, for example, indicated by the greatest uniformity and degree of black (or gray) in the subtracted result—black everywhere in the subtracted image being a perfect gray level match in all areas between two identical images. The subtraction can be of the whole test image at once or on a point to point basis relative to a good panel image, and the subtracted image used to identify defect locations (which would show "bright").

These subtracted images can themselves be operated on, for example, by using the intensity variation techniques below. For subtraction to easily work, the panel should be in substantially the same location for each image, such that any registration error is small, otherwise the effect of mis-registration needs to be removed from the image before the subtraction is made.

It is noted that processing operations such as subtraction, convolution, correlation, etc. can also be done using optical computing techniques using two dimensional light valves, etc. See, for example, "High Technology", January 1985, pp 70. In such applications using coherent processing, a laser source could be used to illuminate the panel (by spreading it through a pin hole creating in the process a true point source). Alternatively, the light valve (spatial light modulator) can create the instant incoherent image detected by a TV camera where spatial modulation can be coherently illuminated and the resultant coherent image processed.

Another image processing technique is to high pass spatial filter the two dimensional DiffractoSight images using convolution or other processing means. Only those areas undergoing change in gray level over more than a predetermined spatial area would be analyzed. This is useful on unknown surfaces since the DiffractoSight image tends to be uniform on locally smooth (undeformed) regions where no data is generally required. The high pass filtered image points up the defect regions immediately which could then be analyzed by grid deviation by matching or by variation in intensity, for example.

For example, the photos of FIGS. 1A, 1B, and 1C clearly illustrate that the degree of dark or brightness and variation therein clearly illustrate the degree of defect seen.

For example, consider FIG. 3A which illustrates a scan of intensity versus position taken through the image of FIG. 1A through section A—A. In the distorted areas, the slope of the distortion is indicated by, and is proportional to, the degree of black (or bright) relative to the light from the normal undistorted surface (shown as a dotted line), with the defect extent given by the area of, and/or the extent in each direction of, the dark (bright) affected region.

The magnitude of the defect and/or its signature can be compared. For example, the rabbit ears defect of FIG. 3B is seen to have a magnitude of 2½ units positive (bright) and 1.5 units negative (dark) relative to the surrounding surface and to have two such bright/dark indications on centers 'C'. Acceptable defects could be judged to be those which do not exceed the values V+ and V− (shown in dotted lines). (Since this car is thought barely acceptable visually in this region.)

Analysis of the two dimensional slope and other features of the distortion is desirable to indicate process changes that can be made to minimize distortion, e.g. in the degree and location of clamping around the edges of the part in a stamping die or in the location of weld guns (whose effects can produce noticeable distortions on the panel surface which can be detected with the invention) and the like.

Another idea is to average the DiffractoSight images of let us say the last 'N' panels (preferably all located substantially the same location to avoid registration errors) and then compare the instant image to the average, e.g. by subtraction. This immediately pin points random defects which would stand out as bright zones. If the average was taken of panels made when panels were "running good" (as on a press line), then the average can provide a better good "master" condition since random noise from whatever source is diminished in the averaged "master" image.

It is noted that the image comparisons can be made instantly, or at a later time from videotapes (or film) made of the DiffractoSight images. In addition, a central processing unit can service numerous stations (each with one or more cameras) in a line or plant (or even multiple plants, via slow scan TV transmission).

For scratch type defects on surfaces as well as small paint bubbles, pits, blisters and other types of defects which are not large in their geometric extent, or represent a surface contrast variation as opposed to a geometric slope change, we have found that the direct on-axis viewing (FIG. 2B) is generally the best since the shadows are reduced. In this case, automation by the image variation or signature technique is most effective.

Therefore, in any one system, one might want to have two sets of sensors, one looking off-axis at the "shadows" indicative of geometrical form defects and the other looking directly on-axis.

In many cases, image processing can be reduced in complexity using a semi-automatic approach or a teach method comparison.

Figure 4:
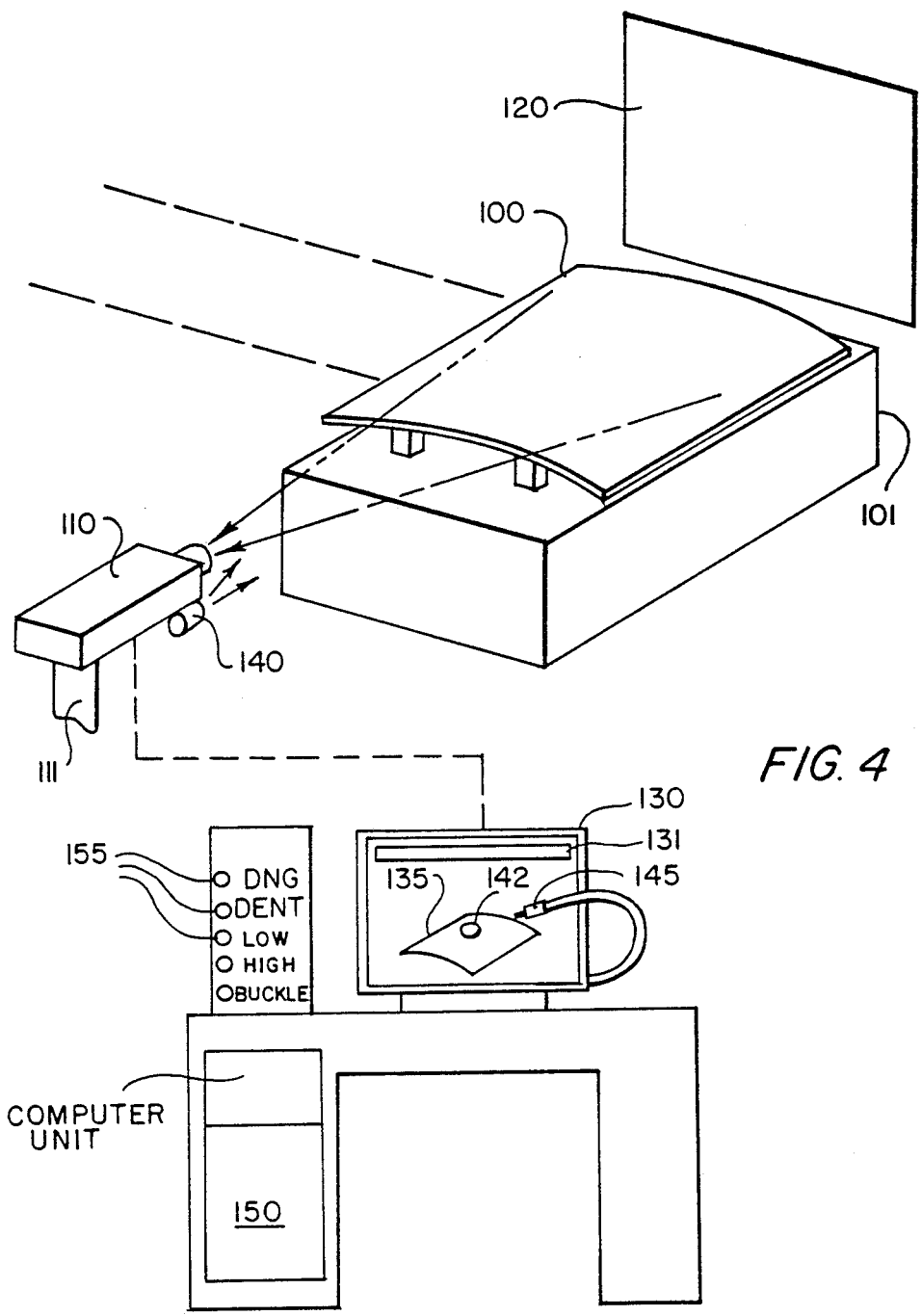
FIG. 4 is an embodiment of the invention used for semi-automatic evaluation of panels.

In the semi-auto case shown in FIG. 4, the data is taken by TV cameras and analyzed with the aid of an operator. The operator in one embodiment looks at the real image (or perhaps even a videotape or time delayed image) of the car body or panel surfaces, selects those areas that he wishes to analyze and instructs the computer what type of defect it is—for example, a "rabbit ears" type distortion around a door handle depression (such as evident in FIG. 1A).

The computer then quantifies, i.e. puts a number on, that defect, applying a predetermined formula for categorizing that defect based on a knowledge of what type it was. A voice recognition system or light pen menu makes a good way to enter the data as to the defect type. For example, the human operator would just simply look at the screen, say "rabbit ears" and the computer would call up the "rabbit ears" analysis program.

This is an easier type of analysis than one which has to find and quantify the defects on the car or panel with no knowledge apriori. However, it should be noted that one generally does have at least some knowledge apriori, namely what panel type it is, where the typical types of defects would fall, and so forth.

For example, on a hood panel with no sharply depressed zones, one would not normally have "rabbit ears" defects. Therefore, that defect would not be possible on that particular part. Even on a door, the "rabbit ears" type of defect occurs only where the door handle depression lies (an area of sharp slope and substantial stretching).

Let us now consider further the operation of the off-line panel checking station, typically located near a press or mold line or further assembly operation.

In this station (shown in FIG. 4), panels 100, plastic or metal, are brought over to a fixture 101 and positioned on the fixture such that they are in essentially the same place each time (in the simplest version). A TV camera unit 110, such as a 1000 line Hamamatsu high resolution type, positioned on a post 111 together with the retro-reflective screen 120, views the panel and creates, on the TV monitor screen 130 (preferably also a high resolution type), a DiffractoSight image 135 of the panel using the light source 140 as shown.

The operator, when looking at this DiffractoSight image of the panel, selects those areas of the panel which are considered to be of importance such as 142 and essentially denotes them with a light pen 145, voice, or other means.

The computer unit 150 then processes the data in the area denoted and displays it on the screen 130 near the defect (or on a separate display). This display as display 131 shown would typically be a severity number. However, in this simplest case, the computer would not be asked to identify the type of defect—this task being performed by the operator.

Operational Sequence—Semi-Automatic Version

1. DiffractoSight image of panel or body side etc. generated on high resolution TV monitor.
2. Operator circles or otherwise denotes defect on monitor screen with light pen and enters which type it is via light pen/menu, voice recognition or other means (e.g. defect classification buttons 155).
3. Additional defects entered, if present.
4. Computer analyzes image in area identified (using gray level variance, grid contour deviation or other means) to determine defect magnitude.
5. Final defect rating calculated considering computer determined value taken in consideration of defect type entered.
6. Defect type and value displayed next to defect on screen (note image held in memory, part can be removed).
7. Data stored (optionally even with complete image) for future reference, where it can be sorted, statistics provided, etc.

Note: Steps 2 and 3 are required only if the panel is unknown. In a teach mode, (described below) the computer is taught apriori where to look first and for what—the operator could simply pinpoint further areas (due to random defects, exceptions, etc.).

A clear follow-on to the semi auto system above is to use basically the same evaluation technology to provide a full automatic analysis with no human operator required. This, as mentioned, can be easier if one sets up the situation to allow analysis of the DiffractoSight image of a known panel type or known section of the body each time, generally possible in most plants. In this way, a "teach" mode can, for example, be implemented (see below).

Before continuing into some of these aspects, let us first address the automotive application areas to which the equipment could be used. On the body these basically are:

1. Body-in-white before metal finish;
2. Body-in-white after metal finish and before paint;
3. Body-in-white after paint or finished car off the line.

In addition to the above, there are panel and sub assembly inspections at virtually every point in the process and these would ideally be located both in the stamping plants and after the panels were assembled into modules.

Defect characterization can be done in several ways. First, the operator could actually make the identification and enter it via a menu on the keyboard or separate pushbutton, voice commands, or the like. The computer would then use this knowledge of what the defect is in order to process the image. In other words, if one knows that it is a certain type of defect, one could, for example, scan across the image in a preferential direction—let us say at 45 degrees, for example, (instead of 0 degrees, represented in FIG. 1A by section AA), and obtain the data as to variation in light level. Different types of sensing operators, processing operators and algorithms might be used depending on which type of defect is present.

Teaching

An alternate method is, in essence, to "teach" the unit what the defect type is. This is especially useful if the panels are always inspected in more or less the same position. For such location it is noted that actual hard fixturing on physical locators may not be necessary for this since guide rails on conveyors or marks or other rough positioners can work sufficiently well for most applications.

In order to teach the system, one could simply place numerous panels of the same type (e.g. Pontiac Fiero hoods) into the checking station and obtain the DiffractoSight image for each. These different "master" panels and their images would desirably contain different levels of severity of a particular defect type that was known to exist for the process in question. This arrangement corresponds to human practice in plants. Inspectors on a line typically look out for certain things and more or less ignore the overall panel in their analysis simply because they know what types of defects that panel is running that day.

Naturally, any gross other types of defects could also be detected so that nothing would get through that was totally out of expectation. It's just that the analysis for numerical ratings of the panel defects would be based on those areas of concern which have been taught, consistent with current plant practice. Large random errors could be assigned a large quality demerit number, with little or no attempt to exactly compare or quantify the result.

The DiffractoSight processing unit would be shown, let us say, three sample images of each expected defect type and location —e.g. mean, max and min. It would then be told that that defect was in the certain location shown and that it was to be evaluated with let us say certain rating numbers. For example, if the minimum defect good panel was desired to cause no demerits, the maximum defect 10 and the mean defect 3, thee would be entered in the computer and further defects of the same type would be essentially "matched" to those images using algorithms developed to essentially correlate the images to the master stored images.

This setup and teaching process would be continued for each defect zone and each panel type of interest. This type of approach has the advantage that processing is based completely on visual perception of the defect as now presently done (i.e. by a critical customer) but has the disadvantage that there is no absolute reference for it (whereas some other forms of processing actually attempt to evaluate the measured deviations of either shadows or grid lines and make absolute evaluations). However, it is not clear at this time that the absolute definition corresponds better to human observation in the ultimate automobile showroom test by the customer, for example, than does the taught matching process.

Increasingly automatic versions of this invention can be provided. For example, if the parts are basically in the same location each time, the zones of interest which are already pre-known as being certain areas of concern, can be automatically processed by the means above. The operator is not required to outline them. Even if the panel was placed on a surface within some sort of limits, let us say oriented ±10 degrees from nominal in the plane of the panel, one still could relatively easily use the same processing algorithms and simply find the panel in space using the computer to correct the image.

This is a needless complication in most instances but could be done. If the panel is substantially rotated, (e.g. 45 degrees), then some of the angles of view of the defects would change and the matching process could collapse, for example.

Operational Sequence—Auto Version Where Defect "Taught"

1. DiffractoSight image generated of panel, body side, etc. located in sufficiently the same place as during teach mode (e.g. within ±3 mm).
2. Computer scans TV image zones taught where characteristic defects lie (e.g. in door handle area for door handle depression "rabbit ears").
3. Defects found in each of areas are quantified according to predetermined weighting criteria for the defect in question, which in a first instance, is assumed to be of the type taught, and/or conditions in each of the inspected areas are matched with gray level images of known defects (min, max, mean, for example) which have been pre-taught for the area.
4. An automatic or other quality index number for the total panel based on the results of step 3 is determined and data recorded.

Note: The steps 3 and 4 can be used to automatically build up a defect history from which mean/max/min data can be continually updated.

The panels brought to this station (and for use with the process in general), must be sufficiently reflective and thus bare metal panels would have to be hilighted with oil or another wetting agent. This would be done typically by hand (in an off-line station) but could also be done with an automatic hilighter located on a robot or at a fixed station.

In the simplest case, hilight can be applied by a robot with a spray gun or by passing the panel on a conveyor under one or more spray guns. In the robot case, the robot after spraying could also carry a camera and light source so as to make the inspection as well.

The processor desirably contains an additional capability to determine if the hilight was insufficient which can be told either by a dullness in the reflective return signal or from an excessive ripple in the image due to too much oil.

Figure 5A:
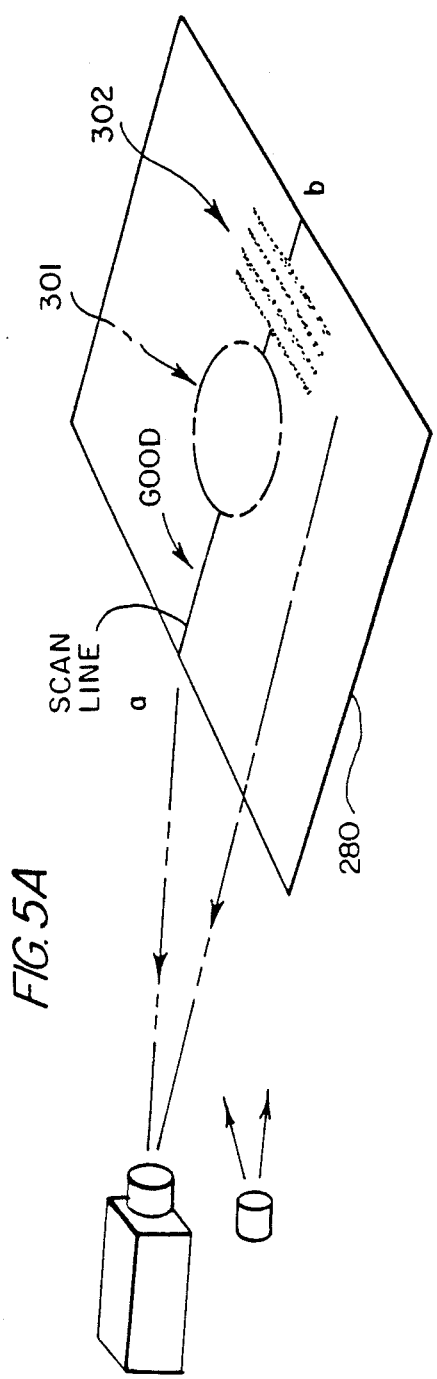
FIGS. 5A and 5B are, respectively, an apparatus for determining if hilight oil is insufficient, excessive, or otherwise maldistributed, and a trace illustrating means for eliminating effects thereof in DiffractoSight images.
Figure 5B:
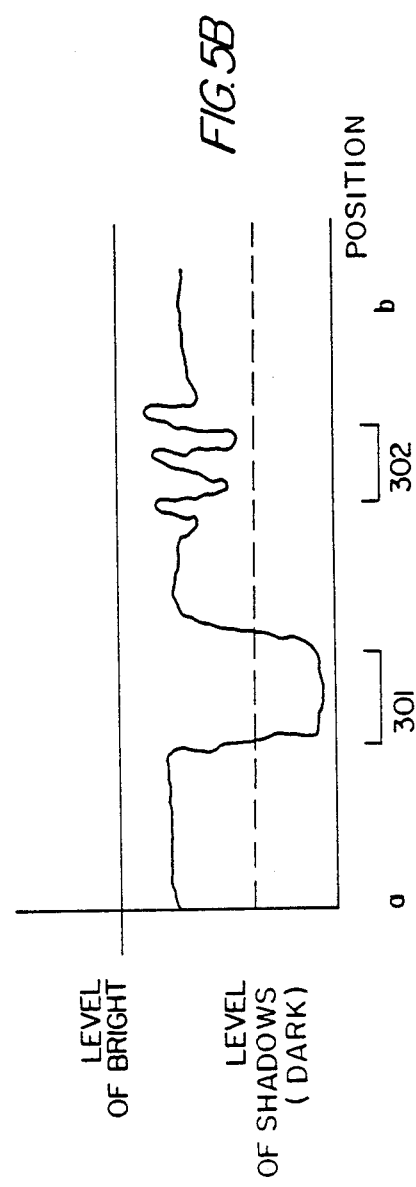

This is illustrated in FIGS. 5A and 5B. A scan a-b is shown through one line of a DiffractoSight panel image of panel 280 containing several conditions—good hilight, lack of hilight, streaks (or bubbles) of hilight.

The analysis system in analyzing TV camera line trace a-b, can perform several functions. First, in the no-hilight zone 301 where reflection is so low that light level drops below a threshold level, the system can in the simplest case, cause this zone, if not too large, to be ignored in processing, so as not to cause a false reject.

A better solution is to cause the zone to be re-hilighted, for example, by commanding a hilight spray robot to spray the zone in question.

Where the panel has excessive hilight resulting in streaking, or bubbles due to foaming, a modulated signal for this zone 302 is produced. If severe, the level of dark or bright it causes can be objectionable and one can either ignore this zone, let it settle out or cause it to be wiped or blown to smooth it out.

While these comments are directed primarily to the hilight application problem, similar affects can result on plastic or other surfaces which may be generally reflective but with spots of dullness.

Rather than ignore the zone, one can also artificially smooth over its image in the computer by assuming it is similar to its neighbour—i.e. shadows or brights or contours. This makes sense especially for small bubbles which are thus removed from consideration in the image.

Figure 6:
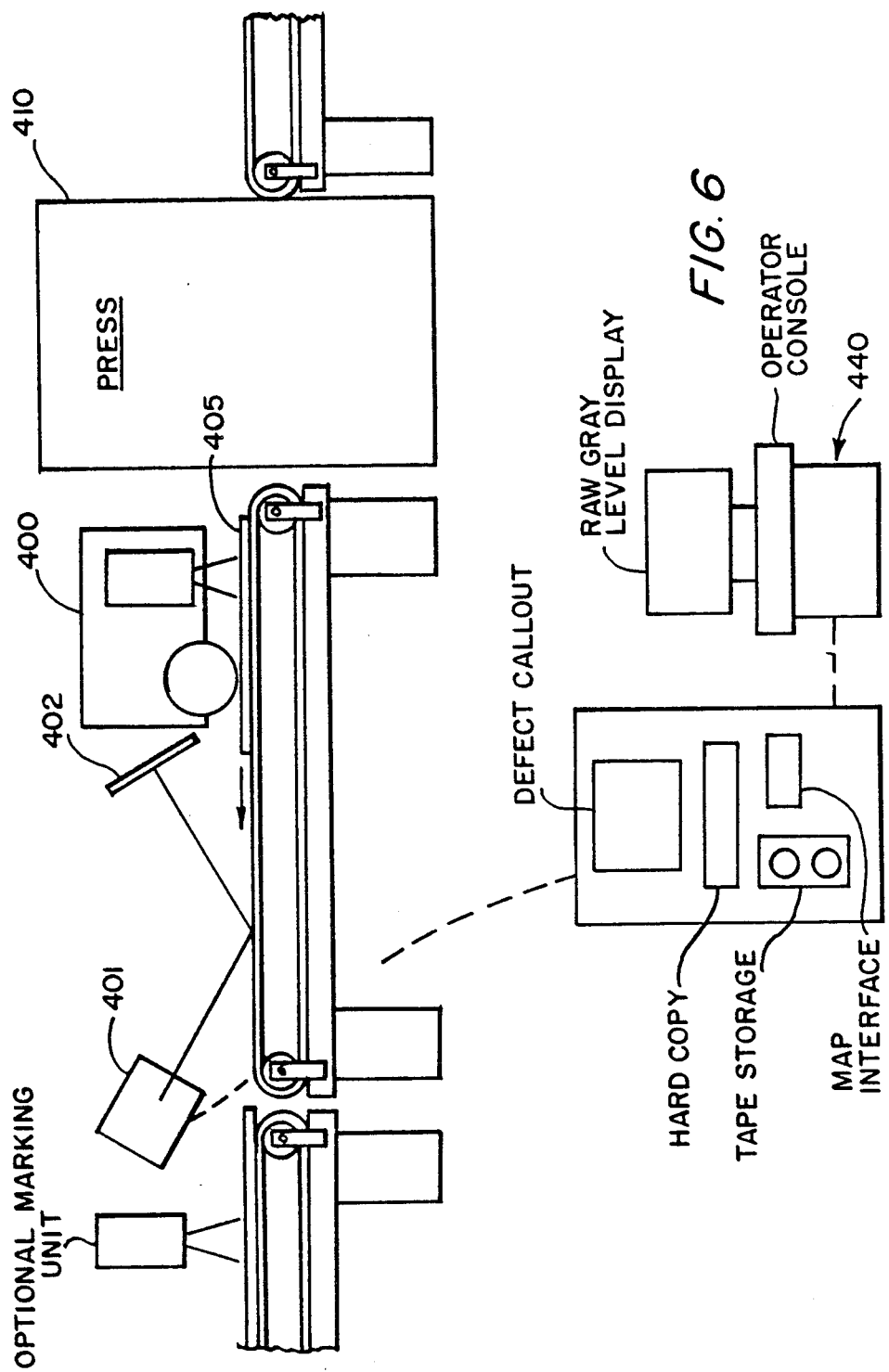
FIG. 6 is an embodiment used for automatic evaluation of panels, including an automatic hilighter.

FIG. 6 illustrates an in-line version of that of FIG. 4. In this case, an automatic hilight unit 400 is utilized and one or more cameras and lights in enclosure 401, depending on the panel 405 in question, and a screen 402 are utilized. Easy changeover results for different parts by simply moving the camera(s) if necessary and calling up a different program for that part.

The automatic hilighter utilizes one or more spray guns to wet the surface. On metal panels coming right out of a press 410, a rotating brush may be utilized to smooth out any drawing compounds, press lubricants, etc. left on the panel. Plastic panels often do not require hilight and could be loaded directly into a fixture such as shown in FIG. 4 by a robot or whatever (that could be off-loading a mold or mold line, for example).

Processing here is performed automatically by computer 440 by any of the means herein described. If defects re-occur in the same location, panel after panel, the press line can be shut down. This is often the case when dirt gets in a die, causing a small ding or dent.

Figure 7:
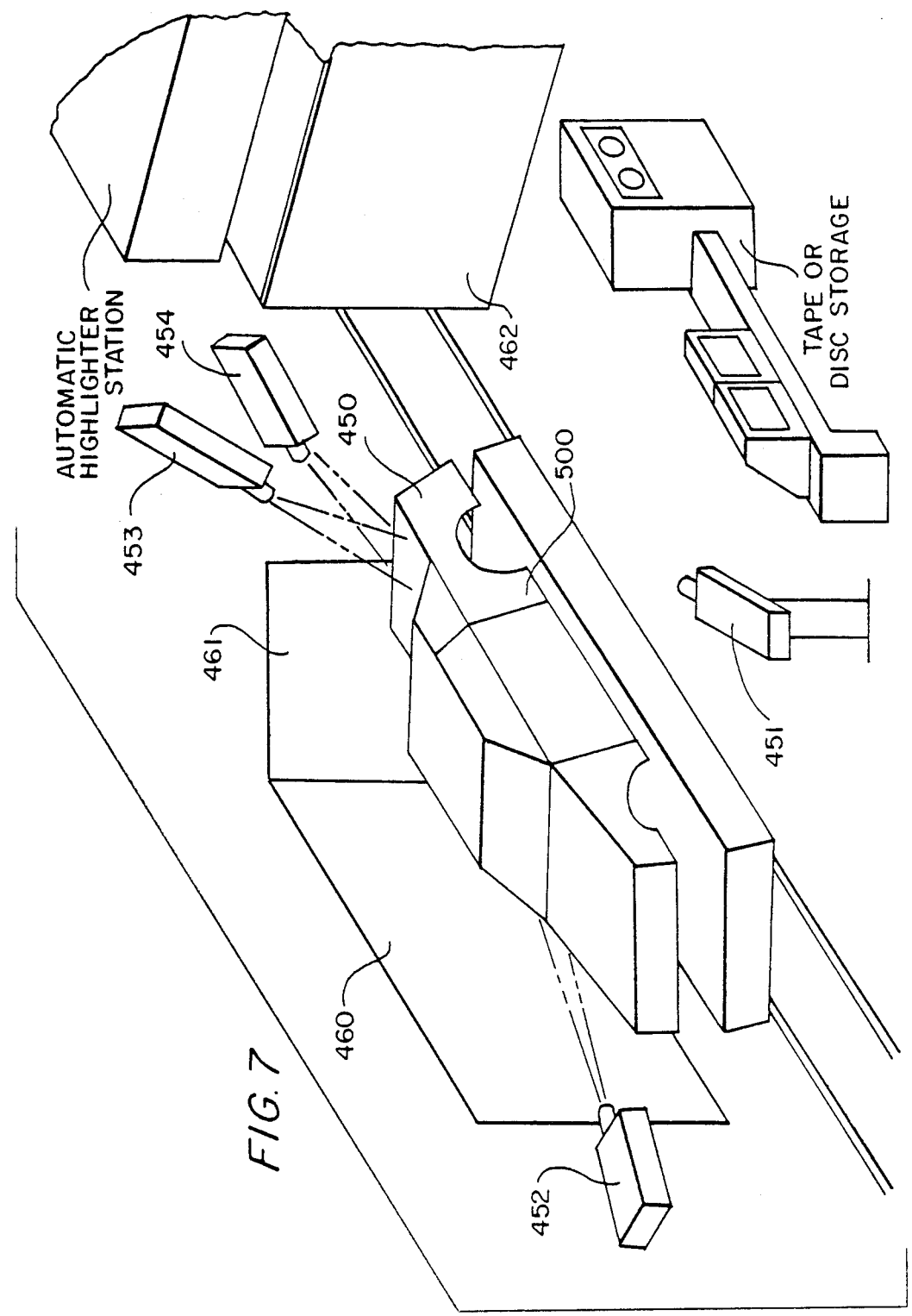
FIG. 7 is an automatic embodiment for car body inspection.

FIG. 7 illustrates an extension of this arrangement to bodie-in-white such as 450 or painted bodies. Basically, the arrangement is the same but there are more cameras (with light sources not shown) such as 451, 452, 453 and 454 to accommodate the increased surface planes to be inspected. Typically three or more cameras are used with corresponding screens 460, 461 and 462 (and TV monitors if manual assist is used). The operator has more time typically to make his analysis (35–40 seconds) than he would with the FIG. 6 in-line panel checking system for example (6–10 sec.), so the additional requirement to view more surface area and planes would not appear a burden. It is noted, however, that operators are not required in the automatic analysis systems herein disclosed.

Once again, an automatic hilighter would be desirable on bare metal surfaces. It is generally sufficient to spray a few percent solution of water soluable oil on the body, a few car lengths back (so it can settle for 30 seconds or more. This wetting agent can be washed off easily so as not to interfere with paint chemistry.

The unit could also print out the defect onto a hard copy which could go with the car alternatively, or in addition it could display at a downstream rework operator's location, a TV image showing the defect area or indeed the whole DiffractoSight image of a panel or body side, say. This could even be a hard copy display of the DiffractoSight TV picture which would travel with the car physically, rather than be transmitted.

As mentioned previously, in a semi-auto mode, an operator could desirably, by voice, light pen, or otherwise, denote what defects he was interested, in which would be computer analyzed, and the rest of the car ignored. He could say what and where too, e.g. door, rabbit ears, fender, dent. He could alternatively point at it on the screen since it is known where it was on the car anyway from what TV frame it was compared to the cars progress.

Note that defects identified can be automatically quantified and only if the defect was severe enough, would its indication be sent ahead to the metal finisher. The indication could include the a DiffractoSight image of the defect to assist the finisher in grinding down or otherwise eliminating the defect. Ideally, a robotic metal finish process could be employed directly using the data obtained.

Image Correlation

The fully automatic generalized system capable of comparing test panels to stored gray level comparison images is more difficult to implement than a taught system. For example, the individual panel is viewed as essentially free of defects unless shadows or light areas occur. If they occur, the zone(s) in which they occur are identified and those areas compared to groups of stored images such as the DiffractoSight images of pre selected known sample panels having buckles, low spots, dings, dents, recoils, waves, "elephant hide", "rabbit ears" and the whole litany of typical types of sheet metal or plastic defects.

Another interesting point, if one looks at an overexposed DiffractoSight picture of the side of a car, one only sees the shadow areas, the rest all being overexposed and white. The shadow areas are the defects. This means that one could purposely over expose and just have the analysis computer find the darker shadow areas (see FIG. 1C). This same result can be achieved in the computer by thresholding the image.

To make the task somewhat simpler, if it is known that the product being inspected, for example, is a metal door, one can simply make the comparison only with those types of defects that would be present on a stamped metal door. For example, the "rabbit ears" type of defect commonly found around door handles, gas tank holes, lock holes on rear deck, etc. would not be found in other areas of those same panels or on other panels such as most hoods at all. Therefore, one would not call up stored images for comparison representing those areas, or at least those panels as a whole.

This becomes still simpler if we know apriori (as is often the case in-plant), not only that it's a door, but particularly say a 1985 Chevrolet Celebrity left front door. Note that the defect configuration would typically be completely different if the door was molded plastic requiring a different set of comparison images. For example, "rabbit ears" defects around door handle depressions do not occur as they are molded in, not pressed.

It should be noted that while computer digital processing is the norm and considered the most probable, these gray level optical images are actually well suited to certain optical correlation techniques which could be employed. In this case, one might not use the TV camera as a pick up means and indeed one could consider even coherent processing where a laser light source was utilized. This is discussed relative to FIG. 9 below.

Other Applications

The invention can also be used to see weld distortions or lack thereof (indicating missed welds), places where strengtheners have been glued, glueing operations and the like. This is because the invention is so sensitive to contour deviations and in this form, it then can act as a non-destructive test procedure.

Data Storage and Tracking

One of the advantages of the invention, both for individual panel inspection coming out of presses, welders, molds, body-in-whites, or painted cars, etc., is that it can be used, not only to quantitatively and qualitatively define the surface flaws, but also to essentially "track" them providing statistical data as well as correlations between certain effects that occur throughout the line.

This tracking function is one of the most powerful aspects of the DiffractoSight technique that it not only allows one to quantitatively accept, reject or statistically audit panels, but it further allows one to very graphically track the production hour by hour, on a panel to panel comparison basis even though the panel itself has been shipped. It is effective largely because it provides a "whole field" image of the panel and its distortions. This tracking can also be automated comparing an instantaneous image to, for example, an average of previous panel images.

The second powerful aspect in this regard is the invention allows comparison of the progress of a panel or other object through a process to identify where defects occur. For example, if such DiffractoSight imaging stations are located throughout an integrated manufacturing process, it is not impossible to think that one could first look at the die blank going into a press (numerous types of steel coil defects have been so discovered, for example roll marks), then look at the panel coming out of the press, again at the same (or a representative) panel after welding, after shipping to the body line, after it is mounted on the body, after metal finish, and after paint.

While total tracking of an individual panel through every station is difficult at the present time, tracking through certain stations can be easily accomplished. In addition, it may not be necessary in general to track every panel or the same panel through the process but simply representative panels.

For example, in a certain 10 or 20 minute time period corresponding to a batch of outer door panels that are welded up to inner panels and shipped to a body plant, if we know that they are from a certain coil that's likely to contain the same defects, and that they're run on the same press that's likely to produce the same defects and runs through the same automatic weld operation that's set up the same through any given, let us say, half hour interval, then we can probably just observe a representative panel of the batch as it goes onto the body.

The types of defects that might be encountered in this are multitudeness, steel defects, press defects, die defects, die wear, dirt in the die, location errors, weld distortions, handling damage, distortion due to addition of trim hardware, damage due to improper metal finish or lack of cleanup in metal finish, etc. DiffractoSight is an extremely powerful technique in providing a clue as to the cause of surface distortion.

Also advantageous is the ability to connect all the data, for example, printing out DiffractoSight data to the repair operators. It could even be a DiffractoSight photograph of the "before" condition printed out and then that compared after repair to see if it's okay or what it is. DiffractoSight images can easily be stored using known means. The very defects that have been called out that day can be stored and, if processed, a quantitative number attached to them. One needn't store the whole side of the car, for example, only the zones with the defects.

Indeed, one can recall the DiffractoSight body-in-white images for later comparison and, for example, those even taken with a similar video setup on tape or otherwise after final paint. With the tracking systems now being put in place in the body and assembly plants, all the tracking programs are there to identify the very body that has been checked when it was in its final painted form and the defects on that body to be correlated so that different degrees of defect condition as viewed on the painted car seen by the customer can be calibrated into the system used on the bare metal body-in-white.

Automatic Processing by Grid Analysis

In the parent application, a method of utilizing the retro-reflective screen and grid pattern deviations was shown. In that application, however, the grid was located at the screen. In other words, grid lines on the screen, either let us say black tape strips put down over a retro screen or conversely strips of retro reflective material, either held in space or pasted to a transparent or black screen, acted as the grid lines whose deviation was monitored by the camera. This particular system, whether it uses a parallel grille or a perpendicular grid of lines, is particularly effective and gives high contrast.

However, we have found in practicing this invention, that it is more convenient, albeit with some less contrast, to generate the grid at the light source projecting it through the surface again to the camera. This yields a double pass grid effect as opposed to the other which is single pass, however, illuminated by the light deviated from the surface in the first place.

While the exact difference in the effects produced between single and double pass grids is not yet known at this writing, the single pass version shown in the parent application has somewhat more contrast. This is presumably due to the spreading that occurs on passing through the surface twice as opposed to once in terms of the grid, but again, this explanation is not clearly known at this time. What is obvious, however, is that by generating the grid at the light source which as defined is for best results nearly a point source, one can utilize very small grids such as those produced by ronchi rulings in a slide projector projected by the slide projector optics. Indeed, a standard 35 mm slide projector with a standard 100 line per inch ronchi ruling was utilized to generate the photographs of FIG. 8A. The substantial deviation in the grid lines around the door handle depression areas which have shown up in FIGS. 1A, 1B, and 1C, is noted. FIG. 8A is overexposed and is the same photograph as FIG. 1C, except for the addition of the grid.

Figure 8B:
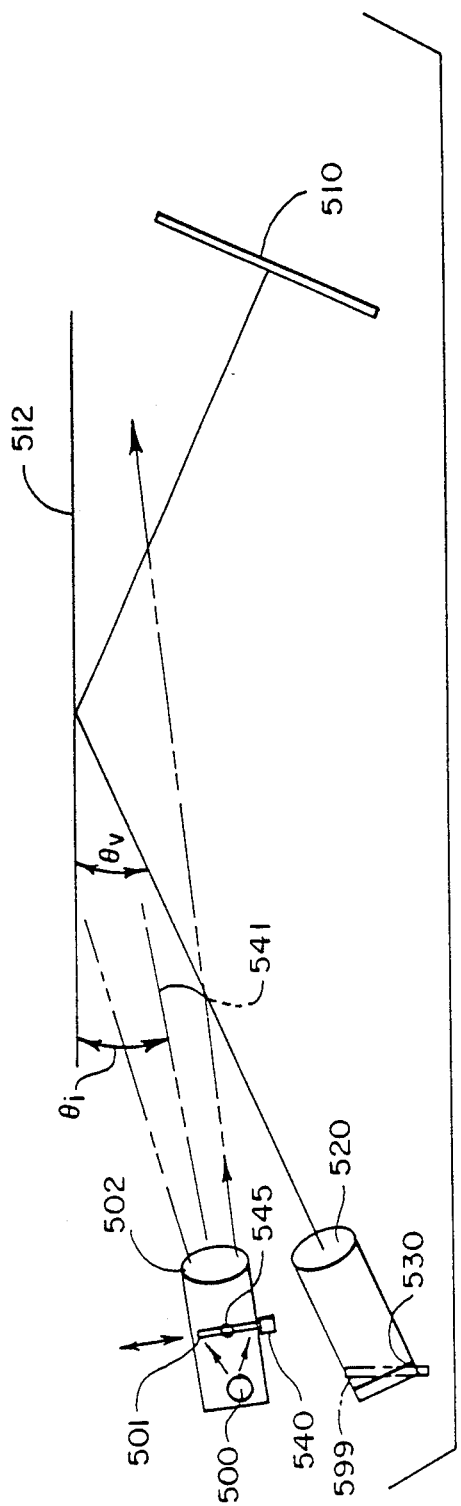
FIGS. 8B and 8C depict apparatus for creating these images.

FIG. 8B illustrates the grid based embodiment according to the invention herein. The basic arrangement is similar to FIG. 2A wherein light is projected from light source 500 through a grid, or in this case, grill, of parallel lines 501 comprised by a ronchi ruling which is imaged by projection lens 502 to be substantially in focus at the reflective screen 510 as well as on the part surface 512. Imaging lens 520 images the part surface so illuminated onto film, TV camera matrix array or other sensing device 530.

The grid projection unit (light source 500, grid 501, and lens 502) can be easily provided by putting a 100 line/ronchi ruling in a slide projector where the slide should be.

When viewed off axis $\theta i \neq \theta v$ (as in FIG. 8), the shadows of the FIG. 1 apparatus are created on the part surface as well, and the distorted grid lines due to the defect appear to modulate the pattern provided.

As shown in the FIG. 8A, a solenoid 540 can be used to move the grid in and out, sweeping the projected grid lines over the surface if desired. The grid can also be rotated about its center line 541 (dotted lines) by means not shown, to rotate the lines on the part surface. Alternatively, it can be rotated about axis 545 in the plane of the ruling so as to effectively change the spacing of the lines on the surface. The grid can also be generated using on-axis illumination ($\theta i = \theta v$) using, for example, beam splitter (not shown for clarity) to direct returning light to a camera.

Figure 8C:
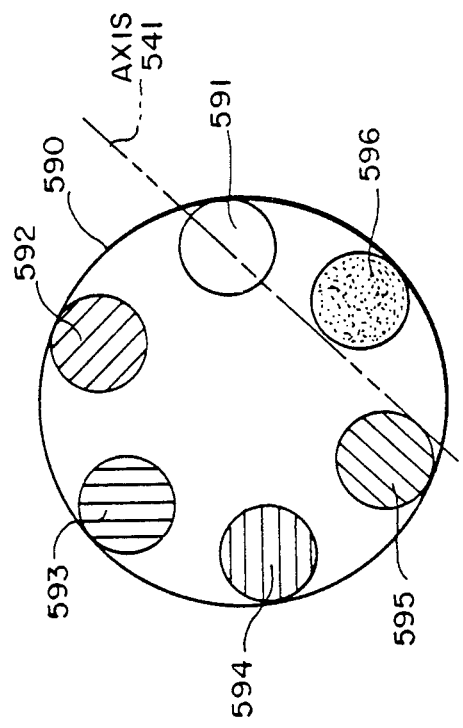

Grid lines can also be rotated, translated, changed in spacing or configuration using, for example, a rotating wheel 590 as shown in FIG. 8C. This wheel can have several positions, each brought sequentially (or by random access) into the projection position of ruling 501.

Illustrated in the various wheel positions are a blank hole 591 (used to produce a FIG. 1 type image), grilles of different tilt angles 592, 593, 594, a cross line grid 595 and a special grid 596 whose lines ar "tailored" for a particular type or size defect (e.g. rabbit ears) condition to allow simpler TV camera scanning. Varying grid spacing or phased grids can also be so used too.

Such tailoring can include making the grille in such a way that concave defects of a certain size cause straight lines in the returned image.

Figure 8D:
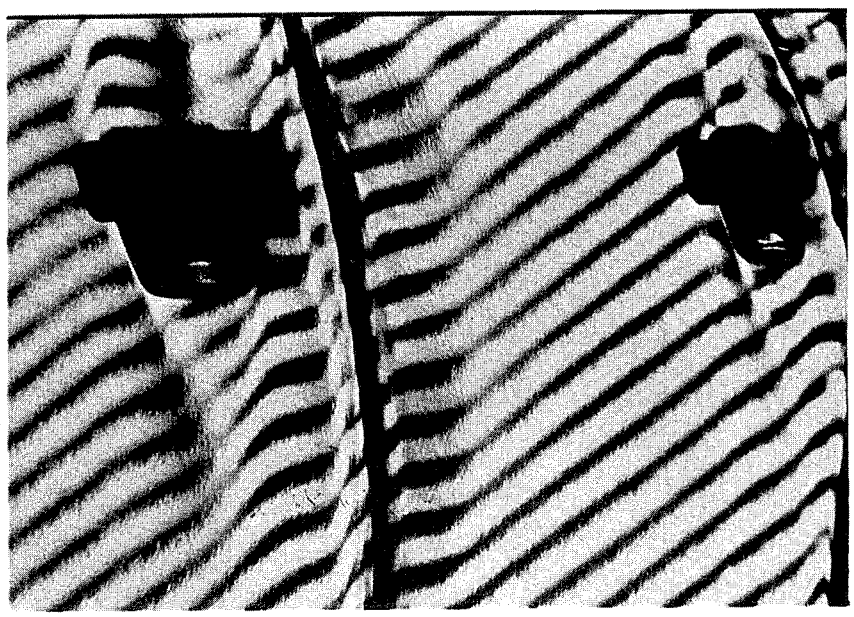
FIGS. 8D and 8E illustrate further use of grids.
Figure 8E:
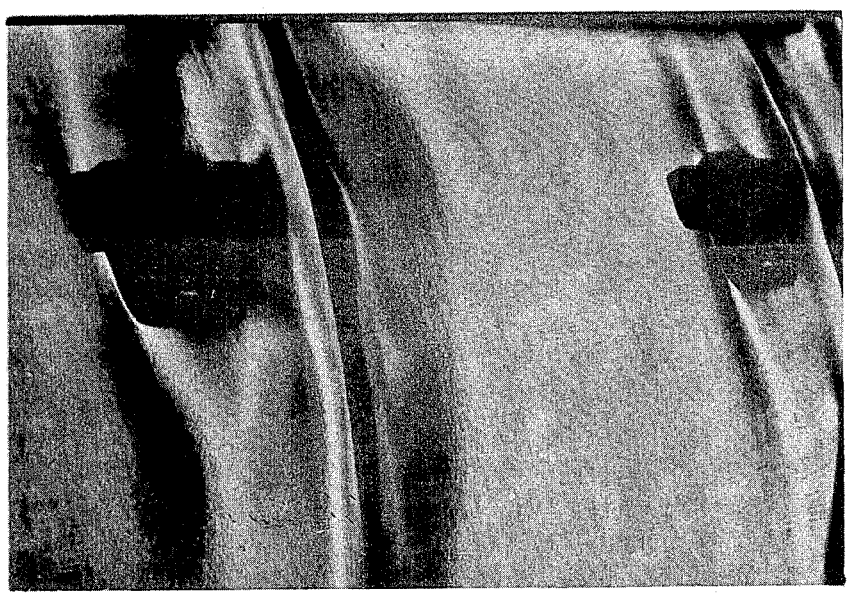

FIG. 8D is a grid similar to FIG. 1B, taken however with the apparatus of FIG. 8B. FIG. 8E is a similar photograph with the grid lines thrown out of focus.

Note that the grid lines and shadows correspond with grid line slopes on bright areas going one direction (at 60 degrees approx. or up to +15 degrees approx. from the 45 degrees approx. grid direction on undeviated surfaces in the picture) and on dark areas going in the other direction (at 30 degrees approx.), or −15 degrees relative to normal grid line direction. Note the local curvature is most pronounced in the "rabbit ear" area. In less defective zones, the slope varies less.

Determination of these localized angular grid lines changes gives local variance in part slope and thence defect severity.

The extension of the part surface over which these slope deviations occur gives the area of defect which can also be used to categorize defects. Indeed, a product can give a weighted answer, for example:

Defect rating = slope variance × (area) × (a constant)

The word "grid" as used herein includes "grilles" or rows of parallel lines, orthogonal grids of perpendicular lines, grids of dots at any other projected pattern which can, in its deviation, indicate local changes of surface curvature.

The FIGS. show grid lines projected approximately at 45 degrees which seems to give the best results on a vertical surface projecting in the horizontal plane, i.e. the grid line projections are relatively 45 degrees to the horizontal plane and to the vertical plane as well in their projection. It is thought that for any given type of defect, in this case the "rabbit ears" type being mostly vertical in its extension, it is preferable to cut this type of defect at some angle, neither perpendicular to it, nor parallel to it.

Clearly, when the grid pattern can be projected with finer spaced lines it would tend to give some improvement in the spatial resolution. In general, it is the edges of these grids that are really letting us see the deviation and the more edges, the closer spaced one could see the deviation of the surface. However, in reality, the finer the grid spacing projected, the more difficult it is to image and contrast difficulties start to arise since the spatial transmission characteristics of the lenses and other elements utilized diminishes.

In addition, it can be seen that even with the relatively coarse 100 line/inch grating used, sufficient resolution really exists to describe most defects, which generally are relatively large in their extension. In short, a very large number of data points is not required and one could easily characterize the "rabbit ears" defect shown in FIG. 8B from the degree of undulation of the grid line shown.

For example, if the grid lines are normally a distance x apart and they deviate in the area of the defect a distance 0.3x say (i.e. a spatial change), we can tell the extent of the defect. For any given optical system, we can also determine defect magnitude from the absolute grid line edge movement in the image, e.g. 1 mm say, at the points of interest. For example:

surface slope variation = K × grid line deviation where K is a constant which is a function of at least the grid orientation angle and optical magnification.

Increased spatial resolution can also be obtained by sweeping the lines across the surface, as noted previously, by moving the grating in either oscillatory, or rotary fashion, or otherwise creating relative movement of grid and surface to allow detection of line location at multiple surface points.

Rotation of the grating in the direction of projection can allow the grating to be in focus over more of the panel surface. The same holds true of the detector array or TV tube in the camera which can be rotated as shown (dotted lines 599).

The idea of using both the grid and the shadow type images in succession is an important feature of the invention. For example, the human eye can very easily see and locate the defects using the shadows, (especially since they tend to exist only where defects occur). However, with the computer it could be desirable to use the grid line deviations to affect the analysis (desirably only where required to minimize processing time).

With the grid system of FIG. 8B, best results in general occur when the grid itself is projected so as to be substantially in focus at the screen, even though the surface is in focus with the camera.

The grid lines in general should be at an angle to the elongation direction of the defect, e.g. between 30 and 60 degrees and preferably 45 degrees approximately as shown relative to the "rabbit ears" door handle defect shown.

Combined systems can be used too. For example, infra red grids that wouldn't interfere with the visual shadow one can be used. Conversely, the grids can be projected or with a separate light source on-axis, illuminating at a different time than the off-axis shadow source. For that matter, one could just have two complete systems with their respective sources and cameras slightly displaced in angle. In general they don't interfere with each other because of the highly directional characteristics of screen material such as Scotchlite 7615.

As has been noted previously, the grids can be oscillated or rotated. Both of these have its features. The oscillation allows moving grid images to be created, accentuating defect locations as the grid lines are swept through it. Tracking of grid line change with time is therefore practical as a measurement means and avoids masking of defects not on a grid line edge that can occur with fixed grids. Note that a moving car or panel passing through a fixed grid field also creates such movement.

Grid rotation not only moves the lines through it, but it also allows different angles of orientation to create different grid deviations which can be of use in evaluating or accentuating different types of defects.

It has been noticed that the grids appear to be relatively unaffected by large contour deviations of the panel presumably due to the retro reflective properties of the screen.

Miscellaneous Points

To eliminate image detail due to small slope defects which are not of interest, one can, as noted previously, simply over expose the photograph or the video image or what have you. In this case, only the darkest shadows show up, those corresponding therefore to the largest defects. The rest are washed out by the over exposure.

Figure 9:
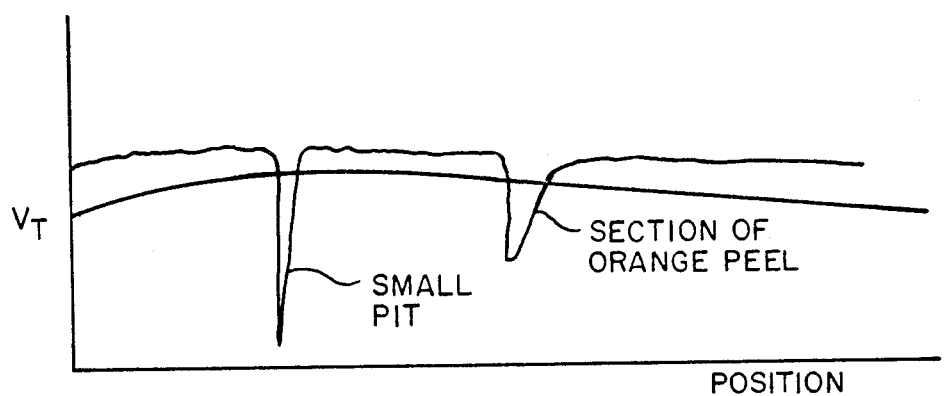
FIG. 9 is an optical computer type method for correlation or image subtraction employed, in general, where panels are in substantially the same position each time.

One can do essentially the same thing in electronic circuits or computer software, setting the threshold of presentation of image areas to the operator. This is illustrated in FIG. 9 where, for example, the zone C of FIG. 3B is compared to either/or thresholds V+ and V— and only images in regions where such thresholds are exceeded are transmitted and/or evaluated.

Such thresholding would desirably operate in a way that would normalize the reflections from the panel on a more local basis rather than an absolute detected intensity such as represented by V+ and V—. In other words, to create a local threshold where only images of panel changes over (or under) a local average by a given amount are presented (together with some preset area around them so interpretation can be made). Alternatively, the whole image can be presented, but with the portions not exceeding the threshold filled in (so as to effectively present only the zones of interest exceeding the threshold).

One could also in the computer determine the extension (e.g. length, width, diameter) of the defect as well, not just its severity or, in this case, darkness (or brightness). Width in this FIG. 3B example is determined by dimension 'M' above threshold V+ and 'N' below threshold V— (roughly corresponding to protrusions, above and depressions below the normal panel surface).

To find defects, one could also look for the tell tail indication of a bright zone along with a dark zone, i.e. the light indication from both slopes of a depression or protrusion defect. This seems to be prevalent on the worst examples. In short, it could be the actual rate of change at the slope—the "peakness" of the defect so to speak from a light level point of view, that is of more importance as opposed to just an absolute base level of black.

In a semi-automatic installation, using human interpretation plus automatic processing, an automatic processor could be operating a a higher magnification than the human viewer since one knows where on the panel one is. For example, the human operator could look at a DiffractoSight TV image of the whole side of the car and even beyond. This would allow him to see the car as it comes through his field of view (as on a conveyor line) and if his attention was diverted momentarily to some other portion of the car, he would not miss anything by returning momentarily to the body side image. As he looks at the side of the car and "light pens" or otherwise signifies where the defect is, the computer which has been looking through a magnified TV image of portions of the car (or other part) simply goes to the TV image stored in memory for that portion, picks it out, and analyzes a zone of it that has been selected. All the previous images can be erased, and refreshed on the next car.

In this context, let us consider a motorized swivelling camera. In this case, assuming the reflective screens are sufficient in extension, one can have a camera that swivels, pointing first at one zone of the car, then at another. This, however, doesn't appear to be compelling from the point of view of processing or viewing since having multiple cameras is relatively inexpensive and quicker.

Another form of moveable camera considered is a robot carried one. This becomes particularly easy if the screens are along the side walls and roof as it would be in the "tunnel" in FIG. 7. (The alternative is where the screen is carried with the camera.) It's easier just to carry the camera and light source and perhaps a simultaneous grid projector and leave the screen fixed.

The robot then would go to the different zones of the panel and look at them possibly from different angles, whatever viewing directions tended to show up the typical defects in that part best. This has the advantage of course of being able to use different angles although a relatively small number of fixed TV cameras might accomplish the same job—if the defect areas were limited. The robot version, however, shouldn't be ignored especially since the robot could be simple, inexpensive and fast. High positioning accuracy (and its cost) is of little importance here.

One advantage of the robot is that it can "home in" on the defect—in other words, point at that defect in question in synchronism with a TV image, for example, spotted by an operator or automatic system and zoom in on it (either physically, by moving the camera or using a motorized zoom lens). One can also have swivelling TV cameras on posts with zooms on them too.

As can be seen from FIGS. 1A, 1B, and 1C, the DiffractoSight image of the window glass is apparent, and thus the reflective distortions in the window glass surface can also be monitored. This is a useful analysis and process feedback tool on float glass lines, for example, where ripples in the surface are caused by waves in the tin bath underlying the glass.

Let us consider now again the DiffractoSight images of FIGS. 1A, 1B, and 1C. It is the variation of light and dark so created that creates the pictures such as the highly realistic and dramatic picture such as shown in FIGS. 1A, 1B, and 1C. These pictures have the apparent illusion that a large light source is illuminating the defects from behind and the "shadows" are being created by the slope defects with the amount of dark and bright indication proportional to the amount of light flux hitting the panel slopes (similar to the eye/brain perception of luminance variation from the snow covered earth surface under sunlight). However, the variation in light intensity with small slope changes seems too great for this to be the only answer.

An investigation as to what causes the "shadows" is still going on at the time of the writing of this application. We know that the initial reflection from the panel of the illumination source creates a pattern of light and dark on the screen, a pattern which is different for protrusion defects than it is for indentation defects, much as would be considered treating the panel as a mirror. The re-reflection of this first reflected pattern back through the surface modifies the situation and the light ray from the surface incident on the screen is re-reflected in an angular bundle from any given point on the screen and, therefore, the re-reflection onto the panel is not the same as the illumination field from the light source.

When the retro-reflective screen is used, however, the power returned when using a point source is quite high and one is able to actually see this for the first time.

After substantial testing it has been found that the smaller (i.e. more point-like) the light source, the more contrast there appears in the DiffractoSight image. However, the source does not have to be a "pure" point to produce good results. For example, the photographs of FIGS. 1A, 1B, and 1C were taken with a linear flash lamp placed such as typically used with thyrister controlled 35 mm camera flash attachments placed parallel to the surface of the panel and apertured to be about 12 mm in length. Making the source shorter than about 12 mm or less than natural 3 mm in diameter doesn't make much improvement and costs light.

We are sure however at this writing, that the smaller the source is, particularly in the direction perpendicular to the surface, the more contrast and the cleaner and the less washed out the pattern will be. However, a large number of workable sources such as those with linear filaments are naturally small and useful.

Another important dimension is the angular spacing of light source and camera in the direction perpendicular to the surface. One theory about the effect is as follows.

One reason for the point source function in producing such shadows can be considered in the following theory of how the effect may be taking place.

Figure 2B:
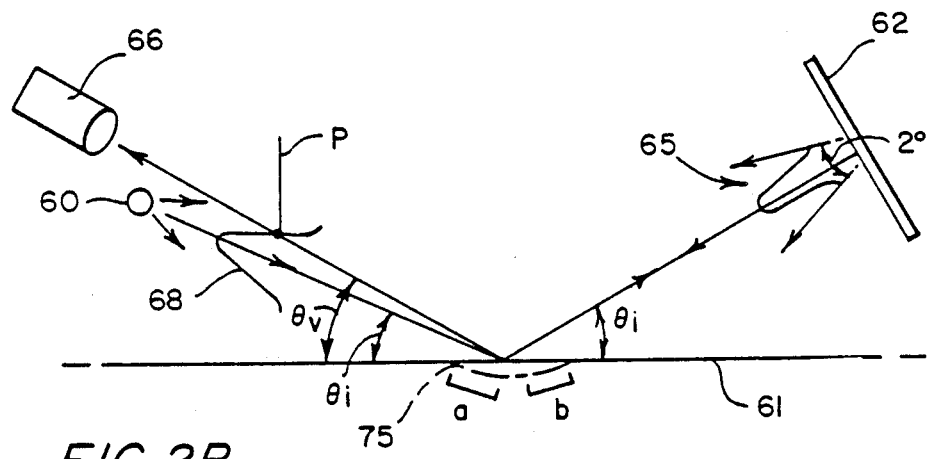

For example, consider FIG. 2B. In this case, light from the source 60 illuminates the surface 61 and screen 62 just as before but it is of use to consider that each zone on the screen filled with the certain number of, let us say, glass beads, re-emits over a solid angle of approximately 2 degrees, let us say.

This re-emission 65 is centered at the incident angle, $\theta i$. Therefore, if as is shown in FIG. 2A, the viewing camera 66 is located at $\theta v$, not equal to $\theta i$, the effective light transmission from each of the points on the screen at that zone is less, as it is modified by the "guassian" (i.e. Bell-shaped) reflectance function of the screen 68, centered about $\theta i$.

Figure 2C:
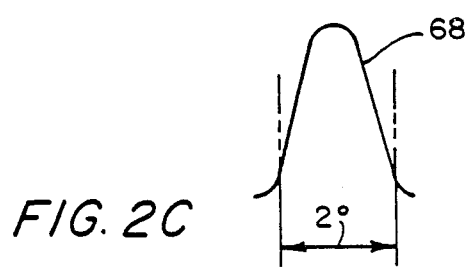
FIG. 2C is a graphical representation of the light distribution on reflection.

Put another way, on a perfect panel with a screen position as shown, the sensing camera unit would not be seeing the maximum level of the light because the light is returning centered in power at angle $\theta i$. Instead, it would be something less, i.e. the amount represented by curve 68 at zone 'P' which is also depicted in FIG. 2C. Naturally, if $\theta v$ is too much different than $\theta i$ so as to fall outside the normal reflectance return of the screen, there is very little light returning which has been found to be the case.

Consider now, however, the effect of a depression 75 (dotted lines) in the surface to this returning light and forgetting for the moment that the light coming from the surface of the screen is modified by the distribution of reflection from the panel on the first pass. The light in this case coming from the screen, if it hits the near side of the depression slope 'A' closest to the observer, it will be angularly shifted so as to move the peak of the reflected intensity toward the observer creating a brighter indication than the surrounding flat surfaces). This is precisely what is seen on the depression point on FIG. 1. Correspondingly, for light hitting the far side of the depression 'B' toward the screen, the slope is in the other direction and the observer sees a darker zone than the surrounding flat surface. Thus slopes 'A' and 'B' are thus converted to light and dark indications, in a very sensitive manner.

This Gaussian illumination theory explains as well the inversion of light and darks which occur if the light source is farther from rather than closer to the surface than the camera (i.e. $\theta i > \theta v$). Zones which are dark become bright and visa versa, as if the apparent light source was near the camera. This is quite workable can seem odd in a live test since the human is aware of the screen's presence which seems like the light source.

The above explanation is a simple one which on the face of it explains the off-axis "shadow" effect and the sensitivity obtained. However, some shadows are seen on-axis but are less apparent as the guassian peak zone is broader than the rapidly changing areas on the steep slopes of the guassian. And too, the light on the screen is not uniform but is itself modified by the effect of the panel on the first pass. The situation is more complicated and under study at the present writing.

Interestingly, somewhat similar lights and darks have been seen in aerial photographs from overhead of rolling terrain on snow covered days with the sun as the source at 30–40 degree angle to surface. In this case, the light and dark conditions are primarily a function of the varied illumination density (watts/CM2) on positive and negative slopes, and the reflection distribution caused by the surface angle and curvature. In these aerial views, however, the slopes needed to cause similar light and dark indications were much greater than those of the car body in FIGS. 1A, 1B, and 1C, say).

Where the defects of interest are of a contrast producing type such scratches or little pits etc. rather than let us say relatively longer wavelength geometric form defects, the relative lack of shadows obtained when $\theta i = \theta v$ is a positive feature since they would tend to obscure such small contrast deviations. For this reason, when one is looking for paint blisters, pits, scratches and other things, it can be desirable to look on-axis ($\theta v = \theta i$). For this reason, dual systems are desirable for many practical applications where in a single camera, two light sources (one on axis, one off) or conversely two cameras and a single light source, would be utilized, operated sequentially to obtain both views.

Again, even in the on-axis case, it still appears that a point source works the best. Processing, however, to find these types of defects is generally done by looking for rapid sloped changes in the detector output such as that shown in FIG. 9.

In one embodiment the defect seen in the TV camera line trace of FIG. 9 is registered as a defect if it drops below a threshold Vt which is proportional to the normal reflectivity of the surrounding surface local to the defect.

It should be noted in practicing either the shadow or grid versions of this invention as shown, the effect of the back reflection from the surface has not been particularly a problem (something discussed in some detail in the parent application particularly relative to the laser scanning version of that application). It is, however, desirable to eliminate the back reflection, that is the reflection of the light source directly from the surface rather than having passed from the retro-reflector screen.

This back reflection can be eliminated by the means previously shown using polarization and the like, but again, the necessity for this has not yet been shown. Clearly, there is little difficulty, for example, in the photographs of FIGS. 1A, 1B, 1C, 8A, 8D, or 8E. More problems can exist on bare metal surfaces.

While at the present time it is thought the screens other than retro-reflective screens of small angular return "beam" spread can also produce the shadowing effects, the difficulties in viewing light reflected from, let us say, a white diffuse screen have made it difficult to study this to date. Indeed, if the "gaussian" theory such as described above (FIG. 2B) relative to the creation of off-axis shadows is correct, it would seem to argue that the shadow creating function would not be anywhere near as good i.e., provide such magnification of small form errors with screens other than those having relatively narrow angular retro-reflective spread functions such as glass bead screens, for example. Indeed, sensitivity would seem a direct function of return spread, however, tests have not been carried out to confirm or deny this.

Quite clearly this invention can be utilized with stroboscopic light sources. In this case, it is desirable to sense the returning light from the surface with a reference detector (or by integrating the camera detector) and cut off the flash duration when a suitable light level (exposure) has been attained. This allows one to normalize the effect for different paint colors, different surface reflectivities, dirty windows on the sensor units and the like. In the case of sources which are non-flash sources, one can use the reference detector output to normalize the light power, the camera detector integration time (exposure time) or aperture size (lens aperture) for that particular surface (detector aperture variation, however, can create other problems and ideally it should be kept fixed with sensor camera integration time or power varied instead).

Because the light intensity sensed by the camera is a function of $\theta v$, it is important that reference or other detector used to sense returning light be located to view along effectively the same axis as viewed by the camera or TV receptor.

Hilight Application

Quite clearly, this invention anticipates that bare metal surfaces or other surfaces which are not normally reflective at the wavelength of light or other electro magnetic radiation used (e.g. IR), would be treated in such a way to make them reflective so that the invention could function.

Typically, with visible light sources and corresponding image cameras and bare steel aluminum or dull plastic surfaces, this is done by applying some sort of a wetting agent onto the surface such as "hilight" oil or oil mixed with water etc. to create a more reflective surface. Indeed, the fluid itself becomes the reflective surface thereof with the fluid essentially following the surface of the part which is to be inspected, filling in the micro roughness.

We have found in our tests that the application of this fluid is really quite simple. It can be sprayed on either using fixed jets or with robots, sprayers, or for that matter, dipped on or wiped on in some fashion so as to wet the surface.

This wetting function is not necessarily required if the light source and camera unit are operable at wavelengths to which this surface microfinish is smooth. It is, for example, possible at infra red wavelengths that such bare metal surfaces can appear to be reflective. For example, a metallic surface of approximately 5 micro inches AA is quite reflective at visible wavelengths of let us say 0.5 microns. If the light source wavelength is increased to 5 microns, the surface can itself be increased to a roughness level of approximately 30–50 AA—that of common sheet metal.

Since most metal surfaces have roughness in the range of 30 AA, it is quite clear that if we could increase the wavelength of the light source into the range of let us say the common CO2 laser wavelength of 10.6 microns, we could operate this invention directly from such surfaces without the use of a hilight fluid.

This invention and the parent application contemplates this and quite clearly the use of such infra red light sources, be they laser or not, coupled with suitable scanning cameras units is of interest.

In this infra red case, a pyrolectric vidicon is of use and one may assume that the TV camera of FIG. 2A could be indeed a pyroelectric vidicon used with an infra red source. The source does not need to be anywhere as coherent (single wavelength) as a laser is. Indeed, a broad band source just as the flash gun used in the photograph of FIGS. 1A, 1B, and 1C is quite acceptable as long as the imaging optics can sufficiently avoid chromatic aberation. This again is more of a difficulty in the infra red than it is in the visible region.

In the infra red (and indeed, a general possibility), it is often of interest to utilize a camera with a single photo detector and a mechanical scanner which essentially scans points in the field of view past the detector. This is typically an arrangement used in many thermal imaging cameras, for example, and given the fact that many of these inspections can occur over relatively long time periods, that is between parts, for example, the fact that it takes awhile to look at the image, like a few seconds, may be inconsequential.

Some of the difficulties in application of hilight solutions are that streaks, droplets, or foam air bubbles appear on the surface. Generally, these problems diminish with time as the oil settles out. In addition all of these effects relative to the shadows created in the DiffractoSight image as shown in FIG. 2A are relatively small and can be eliminated by computer processing or intelligent image processing of the data. This invention includes this possibility and, since in many applications such as the stamped metal body-in-white such wetting agents are required, it is of use to consider means for processing this data to eliminate from the final image processing, whether done by human eye or automatically, effects of the bubbles, streaks, etc., if any, caused by the hilight application.

There are several possibilities. Where the hilight is directly applied, say 5–10 seconds before the actual inspection as is typical on press lines, the problem is not so much lack of oil but of too much oil manifested as streaks or of bubbles in the oil caused by foam in the spray gun. However, if there are clogged jets etc. in spray guns, hilight can be missing manifested as a lack of reflectivity in a certain zone.

Optical Computing

Figure 10A:
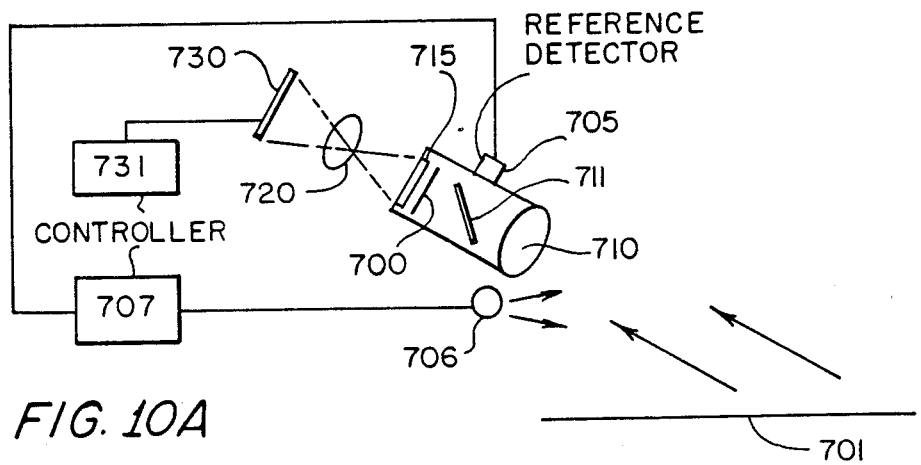
FIG. 10A is a signal processing embodiment of the invention

FIG. 10A illustrates another example of processing of the DiffractoSight image. In this case, however, the computation is made optically, a process which can be done over the whole field image very quickly and, as will be shown, inexpensively.

An excellent review article on this subject appears in *High Technology* issue of January/85, page 69, entitled "Light Modulators Help Crunch Image Data". While the principles involved have been known for decades, the advent of new types of perfected electronic "light valves" or spatial light modulators (analogous to photographic negatives, but with the ability of real-time electronic modulation) are changing the situation.

Put another way, we almost always know the object that we are looking at and its approximate location and orientation. What we don't know and wish to determine, are the defects on that object and particularly their magnitude. Accordingly, the problem, discussed in the referenced article, finding an enemy tank in an image having arbitrary location and orientation isn't really the problem here. Indeed, if the part itself is so mislocated so as to require such techniques to find it, it is not likely, at least for the purposes of inspecting normal product of manufacture such as cars, appliances and so on, that the DiffractoSight image would be of quantitative use. The defects in the image would change considerably in viewing it from different angles and one could have great difficulty comparing images. Almost all relevant production processes allow one to place parts in roughly the same place each time for inspection.

Coherent imaging of the object could be used where the DiffractoSight image is formed using a laser light source. It is easy to do; one simply shines a laser through a pin hole using a spherical lens and one has an instant laser point source. The coherent image could be formed immediately with the returning light.

As shown in the referenced article, one can coherently produce a fourier transform from the TV image taken with incoherent light as well, using a spatial light modulator driven by the TV camera to modulate a coherent light field.

Let us now, however, discuss optical processing of DiffractoSight images using incoherent light. The pictures of FIGS. 1A, 1B, and 1C etc. have all been taken with normal "white" incoherent light and either recorded onto photographic film, looked at visually by eye, or electronically detected using TV camera tubes, matrix array chips and the like. Any or all of these can serve as input to an optical processing step. This optical processing step can be thought of in three ways:

1. To obtain the solution itself; that is comparison of the test image to stored image conditions, desired (e.g. "good" car) or undesired as the case may be.
2. The optical image processing step can be a pre-processing step before final processing by digital computing means.
3. One can digitally preprocess the data, let us say, coming from a TV camera observing the DiffractoSight image before feeding the data to a further optical processing step.

What type of optical processing step would be of use? One such process is to form either a negative or positive image of a desired surface condition and simply see the degree of correlation between the two images.

Optically one can rapidly compare the image of the whole area of the object where only a portion may be defective (thereby indicating which position—i.e. finding the defect). Alternatively, one can consider processing only that portion that is of interest, let us say the area around a door handle depression where a defect either is known to habitually exist or has been found to exist using some other processing means, which itself could be optical, and then isolate it for further processing.

When one looks at the whole image of the object, for example the side of a car in FIGS. 1A, 1B, and 1C, one not only has the sheet metal panel expanses to deal with, but also the edges of the car and other features, such as around the door handle, the windows, etc., that are not generally a subject of the inspection.

In the first processing shown in FIG. 10A, the direct DiffractoSight image 700 from surface 701 has been normalized to be of a constant light power relative to previous images used for comparison, using a reference detector 705 which, in this case, is used to control the light power (or energy if a fixed time exposure) of the projected point source 706 via controller 707. Beam splitter 711 directs light to reference detector 705. Alternatively in other TV based versions, the reference detector also can control a flash source duration or the integration time of the camera, e.g. by activating a shutter, causing the detector elements to be scanned out, etc.

This reference detector normalizes the light power returning which can be a function of the car paint color, degree of hilight oil, dirt on the windows, light power degradation and the like.

The image in this case is formed in the focal plane of the lens 710 and at that point one can either retransmit it through some other stage or simply put a spatially modulated optical image "filter" there 715 which can be re-imaged by lens 720 on let's say a photodetector matrix 730 as shown. This filtered image for example can be in several forms.

For example, if one records a negative DiffractoSight image of the condition of a good car with acceptable defect conditions and uses it as the filter, a "similar" live good car test image will, after transmission through the filter, yield a uniformly gray indication since the areas that were light in the instant image are dark in the filter negative, and visa versa (note gray, rather than near black, results if the average light (governed by the reference detector) in the instant image is biased to be somewhat more intense. This better allows a plus/minus condition (since black in the filter plus almost black in the instant image should ideally provide a discernable non zero detector output).

Obviously however, if the part is not of that condition and particularly one that is defective having a DiffractoSight image comprised of substantial lights and darks, these will come through non-uniformly. If the light power of the instant image is adjusted to be somewhat higher, the amount of deviation from a uniform gray "master" match condition can be looked at with a detector matrix 730, which is interogated by controller 731 to determine the transmitted light intensity values in any portion of the image, to determine where such a variant image exists and the amplitude of variation.

It is noted that other surface condition images can also be stored as master negatives; e.g. max acceptable and min acceptable conditions, various degrees of defects, etc.

Figure 10B:
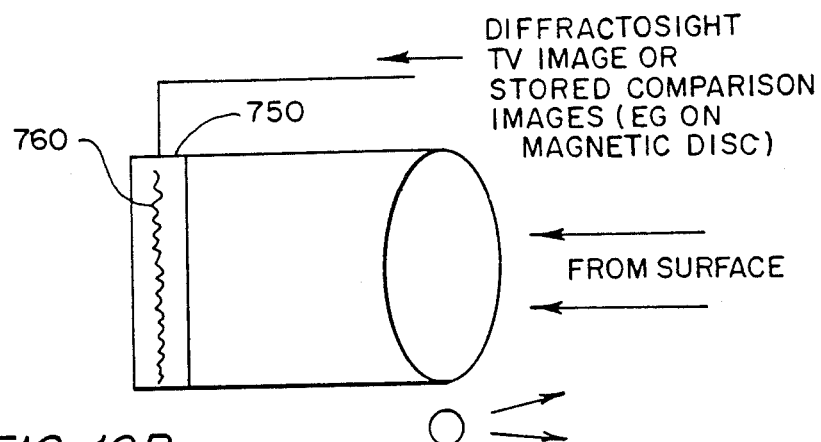
FIG. 10B is an optical computing embodiment of the invention

As shown in FIG. 10B, the processing step can also be done using a light valve 750 in which case the instant TV camera detected DiffractoSight image (or an electronically stored image) from previous embodiments is fed to the light valve which then recreates the image to act as a filter from which further processing can be done optically. In the version shown, an instantaneous "live" DiffractoSight image 760 is formed directly on the light valve 750 which sequentially is fed stored electronic comparison images 715 in a manner analogous in FIG. 10A. Conversely, a "live" TV image can be fed to the valve and processed coherently or against stored filters, etc.

It is interesting to note that certain electronic preprocessing can also occur on the input signals to the light valve, especially on a test image. For example, one can find let us say the variant portion of the image and only transmit it but on an enlarged scale, for example. In other words, there may not be any need to transmit the whole side of the car if only the area around the door handle showed the characteristic deformations of light and dark etc., in which case the door handle zone only would be transmitted to the light valve.

This may be the more useful way of operating such systems—that is to compare only certain zones where the defect is known to exist and one is only trying to quantify, comparing filters stored in memory to see which most correspond to the defect, for example. This, however, can be done in a whole car side basis with different filters in different areas of the negative or the light valve.

One can also note that the filter shown in FIG. 10A can easily be replaced, for example, having a series of such filters on a disk, chain or whatever, so that one does not necessarily have to use an electronically stored filter sequentially fed to a light valve. In the simplest case, one has the usual characterization of marginally bad and good; perhaps for good, really good, mean value of good, marginally bad and really bad, for example. In some cases, representative examples of a few different defect types are required to be compared to identify type as well as severity.

In summation, the optical computing means provides a quick way to compare a whole area of an image to a stored value recorded either photographic film, in video memory for a light valve, or what have you. This stored image is typically of the same panel in different conditions—for example, it could be the average panel run the previous day, it could be a known good or known bad condition, or the like. Relatively simple processing, which in the simplest case can be the amount of light transmitted through the filter in total, then gives the correlation answer.

"Fingerprints"

The DiffractoSight image can be purposely used as a means of reading out deformations which have been put in by other than random manners or for different purposes than let us say inspection and quality control.

One of the uses of this is in the "finger printing" of cars as a method of detecting stolen vehicles. Right now VIN codes (Vehicle Identification Number) are put onto cars and there has been a proposal to put numbers on all the demountable panels of the car subject to thievery by "chop shop" operators.

The disclosed technique could have considerable application since in reality the DiffractoSight image, such as FIGS. 1A, 1B, and 1C of a car body, acts as a sort of "fingerprint".

Let us consider this further. The DiffractoSight phenomena is quite clearly capable of showing up very small form defects. In our relatively limited experience in this sector, we have been able to show stamped panels, even coming off of the same dies, apparently slightly different one from the other (at least when welded up to form a portion of the car).

In any case, let us assume that there is a difference, i.e. that by the time the car reaches the final assembly line, due to the various welding adhesive or other joining operations, handling damage and so on that have distorted or otherwise dented the panel, that the panels are identifiably the same. If the process is completely random and there are enough possible choices, it could be that each panel on a car as originally delivered has its own unique signature which can be viewed easily through the DiffractoSight technique. DiffractoSight equipment could be taken by police officers, for example, to "chop shops" and relatively quickly be used to evaluate panels.

The question is, is this viable? This remains to be seen since obviously damage in use can change the image and whether or not one can see the underlying original signature in the presence of some damage is unknown at this time. It does stand to reason, however, that if the "chop shop" operator damages the part too much to make it undistinguishable, he has also destroyed the resale value of the panel and it is mainly the exterior panels of the car that are most sought after.

This brings up another interesting point; that is, could these panels be changed on purpose such that they would not be objectionable to the eye in the showroom, for example, but would indeed have a unique signature, a signature that, let us say, would not just be a function of random chance but would controlably be fabricated into the panel?

This could be done, for example, by having alterable dies or molds, ones in which small sections of the die or mold were moveable part to part, or batch to batch, whatever is required. Similarly, it could be done, not in the die but in the welding (or joining) operations where inner and outer panels would be welded in such a manner to deform the panel slightly in certain areas on purpose. Similarly, adhesive application variation would do this too.

This procedure could be roughly equivalent to writing a number on the part. For example, a code could actually be put in using deformable membranes or other positionable surfaces incorporated in a mold, die, etc. that could be selectively deformed by capacitive action or what have you to provide a unique "number" or code for that panel.

Typically such membranes have been used for phase light modulators and indeed one is discussed in the referenced article on optical computers. If the membranes distort enough (e.g. 5-10 microns depth), these distortions show up in the stamped or molded part and thence in the defect as DiffractoSight image pattern changes. Thus the DiffractoSight image is a method of reading out these modulated inputs. Indeed, one could use small deformable or positionable surfaces in the welds or dies to actually cause a serial number to be stamped or molded into the part so finely as to be substantially only readable with DiffractoSight and not objectionable to the customer. One could also use DiffractoSight as a method of reading deformed membranes for whatever purpose (as in optical computing).

One problem in looking at the whole car body side as in FIGS. 1A, 1B, and 1C, is the intensity changes that occur from one end of the car to the other. For this reason, it may be desirable to look at more limited areas, particularly in the direction of light projection allowing one to keep the panel in focus, as well as the light level more constant. For example, in any one area over the rear door, the light level is reasonably constant. Otherwise, however, correction programs can be utilized to correct in software or in hardware, the light to normalize it over the surface if desired.

Clearly, a unit can be built attached to the end of a robot or in an in-line application where the screen and the camera unit are physically connected. While this creates a much larger scanning head, it does fix the angles etc. and allows the robot to move the sensor around in a unitary manner without regard to worrying what's in the surrounding area.

Carrying the unit such as camera, light source and screen on a robot, for example, or even just using a fixed screen off the robot carrying the sensor and camera unit and looking at a small zone at one time, allows one to specialize the magnification toward a particular zone in question and process the data for that zone at any one time.

Such a scan occurs in a natural fashion if a panel is swept underneath a sensor unit where it could make sense to have, as in the parent application, several sensor units across a panel looking at each zone in succession as the panel moved under it. This would be obviously at somewhat higher magnification.

The invention can also use a partially reflective surface added to the front of either the grid projector (FIG. 8B) or, in the case of the shadow based DiffractoSight image, to a partial reflector in front of the light source. This allows a multiple pass phenomenon to take place, where the light is reflected back and forth between the screen and the partial reflector. This can, under certain circumstances, increase the sensitivity but requires careful alignment of the reflective surface perpendicular to the line of sight of the projection unit. Since the retro-reflective screen sends back the majority of the energy back along the same path, several passes can exist before the light is degraded to nothing. For this purpose, a strong light source such as a high powered halogen or flash lamp is desireable with a 50% or more reflective mirror for example.

Other new developments in the invention since the parent disclosure:

First it is generally necessary for best results to use two eyes or two cameras stereo fashion as was discussed relative to FIG. 6 and FIG. 7 of that application. A single light source and camera such as 600 and 601 (or 710, 720) in that application works well for most purposes.

Similarly, the concern over direct back reflection from hilighted bare metal surfaces is not as important as once thought. The invention is quite useable even without means to reduce these reflections (better results however do occur if they are reduced).

It is noted that the invention is also useful for repair of car bodies and other "skins" on aircraft etc., to assist in rapidly obtaining a good surface condition by grinding or smoothing in the right places. This is also true in die or mold manufacture where DiffractoSight analysis of the part provided or the tool itself can provide information on what to correct.

Finally, it goes without saying that screen material should be sufficiently large such that light bouncing off a panel will hit the screen and return for highly curved panels. It may also be desirable to curve the material, to keep the surface of the material in approximate normality to the light incident on it from the panel. This is a good feature because the screen material does vary in its retro-reflective properties with angular incidence direction—especially as one gets far away from normality.

Such considerations can also occur when deep dents occur locally in a surface, causing large (e.g. 10 degrees or greater) surface slope variations. This causes a two times change in the direction of attack to the screen and can cause, in severe cases, the light to miss the screen altogether.

What is claimed is:

1. A method of inspecting a surface comprising the steps of:
   illuminating an extensive area of the surface with light by directing light onto the surface area in such a manner that the light is reflected therefrom;
   providing a retroreflective member comprising a large number of small retroreflective elements in a position such that light reflected from the extensive illuminated surface area impinges thereon, is then returned to the illuminated surface area, and is re-reflected therefrom;
   imaging light re-reflected from the extensive illuminated surface area;
   scanning the imaged light to determine intensity variations in that imaged light, and determining from the intensity variations in the imaged light a characteristic of said surface.

2. A method according to claim 1 wherein the light used in illuminating of said area of the surface is directed along an axis which is angularly displaced from the axis of said imaging so as to form bright or dark regions characteristics of form defects on said surface.

3. A method according to claim 2 wherein the light used in illuminating said area is directed along an axis which is closer to said surface than the imaging axis.

4. A method according to claim 1 wherein illuminating said area is carried out using a light source and said surface and said retroreflective member are substantially greater in dimension than said light source.

5. A method according to claim 4 wherein illuminating said area is carried out using a said light source which is substantially a point source.

6. A method according to claim 1 wherein a rating number for said intensity variation is further generated proportional to the degree of dark (bright) signal below (above) a threshold value.

7. A method according to claim 6 wherein said threshold value is determined relative to an average value of image intensity in the region of said defect.

8. A method according to claim 1 wherein said scanning step is carried out using a TV camera.

9. A method according to claim 1 wherein said inspection includes substantially determining any deviation in the local geometric form of said surface.

10. A method according to claim 1 wherein scratches, pits, listers, runs and other blemishes and distortions of small dimension in said surface are inspected.

11. A method according to claim 1 wherein illuminating said area is carried out using projected light in the form of a pattern of one or more lines, and the determining step includes determining the local deviation in said lines caused by a distortion in said surface.

12. A method according to claim 11 when the deviation in at least one edge of at least one of said lines is determined.

13. A method according to claim 1 wherein the imaging step provides that said surface is substantially in focus in said image.

14. A method according to claim 11 wherein illuminating said area is carried out using a said pattern which is a grille or grid of parallel lines.

15. A method according to claim 11 wherein illuminating said area is carried out using a said pattern which is rotated to maximize the effect of surface distortion and/or facilitate said determination.

16. A method according to claim 11 wherein illuminating said area is carried out using a said pattern which is oscillated to cause said lines to sweep through at least a portion of a distortion on said surface.

17. A method according to claim 14 wherein the projection of said grille or grid is zoomed in and out to change the density of lines on said surface.

18. A method according to claim 11 wherein a distortion rating number is further generated proportional to the degree of deviation of said lines.

19. A method according to claim 18 when a said rating is generated which further includes consideration of the area over which deviations above a given value exist.

20. A method according to claim 1 wherein a said retroreflective member is used in returning the light to the illuminated surface which comprises a substantially dense distribution of glass beads.

21. A method according to claim 20 wherein said retroreflective member is used in returning the light to the illuminated surface which comprises beads in a diameter range 20–150 microns.

22. A method according to claim 20 wherein a said retroreflective member is used in returning the light to the illuminated surface which comprises glass beads of a size that is essentially uniform within a 30% variation on said screen.

23. A method according to claim 1 wherein said determination step includes comparing gray level images of said surface or portions thereof to at least one stored image.

24. A method according to claim 23 wherein a plurality of said stored images are used and said stored images represent images taken of similar part surfaces having varying levels of distortion severity.

25. A method according to claim 24 wherein said part surfaces are located in a uniform location such that comparison can be easily made.

26. A method according to claim 1 wherein said imaged light is imaged on an image sensor and a light source used to illuminate said surface is pulsed to "freeze" the image of said surface on said sensor.

27. A method according to claim 1 wherein said imaged light is imaged on an image sensor and said surface is in motion relative to said sensor.

28. A method according to claim 23 wherein at least one stored image is subtracted from the actual image.

29. A method according to claim 1 wherein said determination step includes thresholding said imaged light to provide only the most black and/or bright area relative to the surrounding panel image being compared.

30. A method according to claim 1 wherein said determining step includes considering the part type whose surface is under inspection and calling from memory the determination steps required to inspect at least a portion of said part.

31. A method according to claim 30 wherein the image of at least a certain portion of said part is compared to stored images characteristic of distortion types which can exist on said part within said portion.

32. A method according to claim 31 wherein a correlation with said stored images is performed and the degree of correlation indicates the distortion type or severity.

33. A method according to claim 1 wherein said determination step includes consideration of spatially variant portions of said image within a certain band.

34. A method according to claim 33 wherein said band does not include high frequencies such as those of edges in said image.

35. A method according to claim 34 wherein said band does not include the DC component having effectively no spatial variance in light intensity.

36. A method according to claim 1 wherein said determining step includes convoluting said image.

37. A method according to claim 1 wherein said determining step first includes the step of enhancing the contrast of said image in at least an area of interest.

38. A method according to claim 1 wherein said imaged light is recorded and said determination step is performed at a later time.

39. A method according to claim 38 wherein a plurality of images of different examples of the same type are recorded.

40. A method according to claim 39 wherein said plurality is averaged to form an average image.

41. A method according to claim 40 wherein said averaging step occurs performing a preprocessing step on each image.

42. A method according to claim 40 wherein a test image is subtracted from a stored image to determine differences between the two images.

43. A method according to claim 1 wherein said surface is alterable in its geometric form by electronic, mechanical or other means.

44. A method according to claim 1 wherein said determining step includes optical comparison of the image produced in said imaging step with stored images or other spatially variant patterns.

45. A method according to claim 1 wherein said determination step comprises determining, from the intensity variations in the imaged light, geometric distortion of said surface.

46. An apparatus for inspecting a surface comprising:
illuminating means for illuminating an extensive area of the surface by directing light onto the surface area in such a manner that light is reflected therefrom;
a retro-reflective member comprising a large number of small retro-reflective elements positioned relative to the surface such that light reflected from the extensive illuminated surface area impinges thereon, is then returned to the illuminated surface area, and is re-reflected therefrom;
imaging means for imaging light re-reflected from the extensive illuminated surface area;
scanning means for scanning the imaged light to determine intensity variations in that imaged light; and
detecting means for determining from the intensity variations in the imaged light a characteristic of the extensive illuminated surface area.

47. An apparatus as claimed in claim 46 wherein said detecting means comprises means for determining from the intensity variations in the imaged light, geometric distortion of the extensive illuminated surface area.

48. An apparatus according to claim 46 wherein the axis of illumination of the surface is angularly displaced from the axis of said imaging so as to form bright or dark regions characteristic of form defects on said surface.

49. An apparatus according to claim 48 wherein said illumination axis is closer to said surface than said imaging axis.

50. An apparatus according to claim 46 wherein said illuminating means comprises a light source and wherein said surface and said retro-reflective member are substantially greater in dimension than said light source.

51. An apparatus according to claim 50 wherein said light source comprises a substantially point source.

52. An apparatus according to claim 46 further comprising means for generating a rating number for said intensity variations which is proportional to the degree of dark (bright) signal below (above) a threshold value.

53. An apparatus according to claim 52 wherein said threshold value is determined relative to an average value of image intensity in the region of a distortion in the surface.

54. An apparatus according to claim 46 wherein said scanning means comprises a TV camera.

55. An apparatus according to claim 46 wherein said detecting means comprises means for substantially determining any deviation in the local geometric form of said surface.

56. An apparatus according to claim 46 wherein said detecting means comprises means for inspecting scratches, pits, blisters, runs and other blemishes and distortions of small dimension in said surface.

57. An apparatus according to claim 46 wherein said illuminating means comprises means for projecting light in the form of a pattern of at least one line, and said detecting means comprises means for determining local deviations in said at least one line caused by a distortion in said surface.

58. An apparatus according to claim 57 wherein said detecting means determines the deviation in at least one edge of said at least one line.

59. An apparatus according to claim 46 wherein said surface is substantially in focus in said image.

60. An apparatus according to claim 57 wherein said pattern comprises a grille or grid of parallel lines.

61. An apparatus according to claim 46 wherein said pattern is rotated to maximize the effect of surface distortion and/or to facilitate the determination made by said detecting means.

62. An apparatus as claimed in claim 57 wherein said pattern is oscillated to cause said at least one line to sweep through at least a portion of a distortion in said surface.

63. An apparatus according to claim 60 further comprising zoom means for zooming the projection of said grille or grid in and out to change the density of lines on said surface.

64. An apparatus according to claim 57 further comprising means for generating a distortion rating number proportional to the degree of deviation of lines of said pattern.

65. An apparatus according to claim 64 wherein said rating further includes consideration of the area over which deviations above a given value exist.

66. An apparatus according to claim 46 wherein said retro-reflective member comprises a screen composed of a substantially dense distribution of glass beads.

67. An apparatus as claimed in claim 66 wherein said beads are in a diameter range of 20 to 150 microns.

68. An apparatus according to claim 66 wherein the size of said glass beads is essentially uniform within a 30 degree variation.

69. An apparatus according to claim 46 wherein said detecting means includes means for comparing gray level images of said surface or portions thereof with at least one stored image.

70. An apparatus according to claim 69 wherein a plurality of stored images are used and said stored images represent images taken of similar part surfaces having varying levels of distortion severity.

71. An apparatus according to claim 70 wherein said part surfaces are located in a uniform location such that a comparison can be easily made.

72. An apparatus according to claim 46 wherein said illuminating means comprises a light source, said scanning means includes an image sensor and said apparatus further comprises means for pulsing said light source to "freeze" the image of said surface on said image sensor.

73. An apparatus according to claim 46 wherein said scanning means includes an image sensor and wherein said surface is in motion relative to said image sensor.

74. An apparatus according to claim 69 wherein said detecting means includes means for subtracting at least one stored image from the actual image.

75. An apparatus according to claim 46 wherein said detecting means includes means for thresholding the imaged light to provide only the most black and/or bright areas relative to a surrounding panel image being compared therewith.

76. An apparatus according to claim 46 further comprising means for recording the imaged light, said detecting means acting to determine a characteristic of said surface based on the recorded imaged light at a time later than the recording thereof.

77. An apparatus as claimed in claim 76 wherein a plurality of images of different examples of the same type are recorded by said recording means.

78. An apparatus according to claim 77 further comprising means for averaging said plurality of images to form an average image.

79. An apparatus as claimed in claim 78 further comprising means for performing a preprocessing step on each image before averaging of said image by said averaging means.

80. An apparatus according to claim 78 further comprising means for subtracting a test image from a stored image to determine differences between the two images.

81. An apparatus according to claim 46 further comprising means for altering the geometric form of said surface.

* * * * *